(12) United States Patent
Palmer et al.

(10) Patent No.: US 6,271,039 B1
(45) Date of Patent: Aug. 7, 2001

(54) COMPOSITION FOR USE IN FLUORESCENCE ASSAY SYSTEMS

(75) Inventors: Derek Adeyemi Palmer, Farnborough; Martin Thomas French, Quorn, both of (GB)

(73) Assignee: Kalibrant Limited, Leicestershire (GB)

( * ) Notice: Subject to any disclaimer, the term of this patent is extended or adjusted under 35 U.S.C. 154(b) by 0 days.

(21) Appl. No.: 09/355,467

(22) PCT Filed: Dec. 15, 1998

(86) PCT No.: PCT/GB98/03750

§ 371 Date: Jul. 30, 1999

§ 102(e) Date: Jul. 30, 1999

(87) PCT Pub. No.: WO99/34219

PCT Pub. Date: Jul. 8, 1999

(30) Foreign Application Priority Data

Dec. 24, 1997 (GB) .................................................. 9727355

(51) Int. Cl.[7] .................................................. G01N 21/64
(52) U.S. Cl. .............................................. 436/166; 436/172
(58) Field of Search .................................. 436/166, 172; 422/61, 82.08; 435/21

(56) References Cited

U.S. PATENT DOCUMENTS

| | | | |
|---|---|---|---|
| 4,451,563 | * 5/1984 | Kaufman | 435/21 |
| 4,666,862 | * 5/1987 | Chan | 436/501 |
| 5,011,964 | * 4/1991 | Mynarcik et al. | 558/179 |
| 5,209,776 | 5/1993 | Bass et al. | 106/124 |
| 5,292,362 | 3/1994 | Bass et al. | 106/124 |
| 5,387,525 | * 2/1995 | Munkholm | 436/111 |
| 6,110,749 | * 8/2000 | Obremski | 436/527 |

OTHER PUBLICATIONS

Huang, et al., "A Sensitive Competitive ELISA for 2,4–dinitrophenol using 3,6–fluorescein diphosphate as a fluorogenic substrate," *J. Immunol. Methods*, 149:261–266 (1992).

Kapoor, et al., "Fluorescence and Absorption Spectra of Rose–Bengal Dye in the Presence of Surfactants," *J. Lumin.*, 22:429–439 (1981).

Mishra, V. N., "Influence of Surfactants on the Fluorescene and Absorption Spectra of Eosin in Aqueous Solution," *Acta Chim. Hung.*, 116:5–12 (1984).

Ströhl, G. W. and Kubzak D., "Absorptionsspektren and Beständigkeit der Aniontensid–Methylenblau (Methylgrün)–Komplexe," *Fresenius Zeitschrift Fuer Analytishe Chemie*, 242:88–92 (1968).

* cited by examiner

Primary Examiner—Jeffrey Snay
(74) Attorney, Agent, or Firm—Heslin & Rothenberg, P.C.

(57) ABSTRACT

The present invention relates to a composition for use in fluorometry, a method of fluorometry and the use of a class of new reagents in fluorometry. The composition comprises a substrate which is a non-fluorescent derivative of a fluorophore, and a shifting reagent which shifts the absorbance wavelength maximum of the fluorophore which maximum is naturally above 450 nm. The shifting reagent is present in an amount predetermined to shift the maximum to a preset value.

19 Claims, 17 Drawing Sheets

Synthesis of naphthofluorescein phosphate

Naphthofluorescein   Naphthofluorescein diphosphate

Purification profile pf naphthofluorescein diphosphate (A) and monophosphate (B)

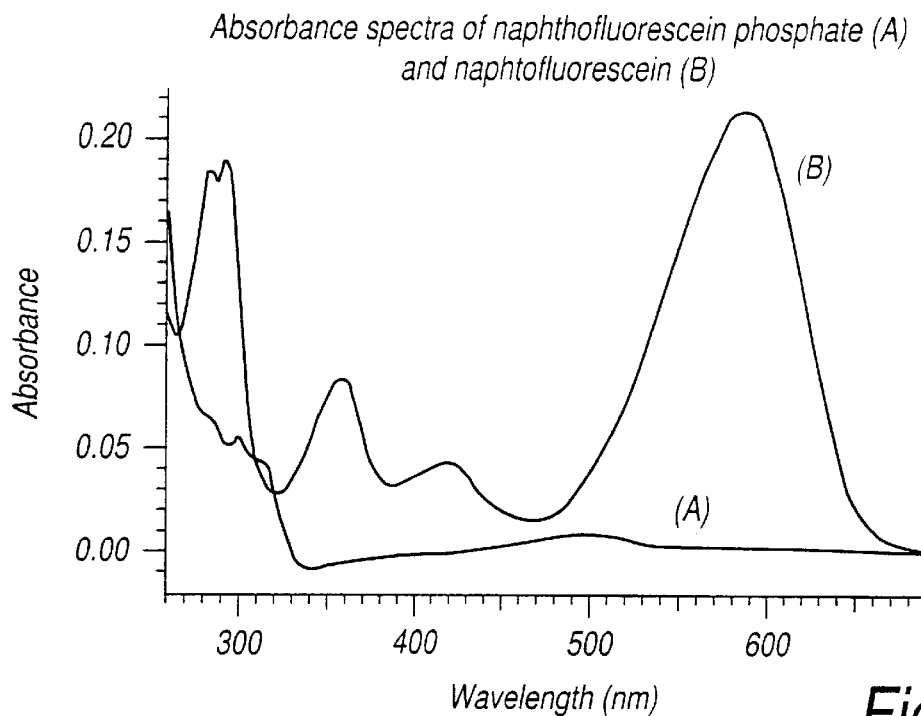
Fig.3 Absorbance spectra of naphthofluorescein phosphate (A) and naphtofluorescein (B)
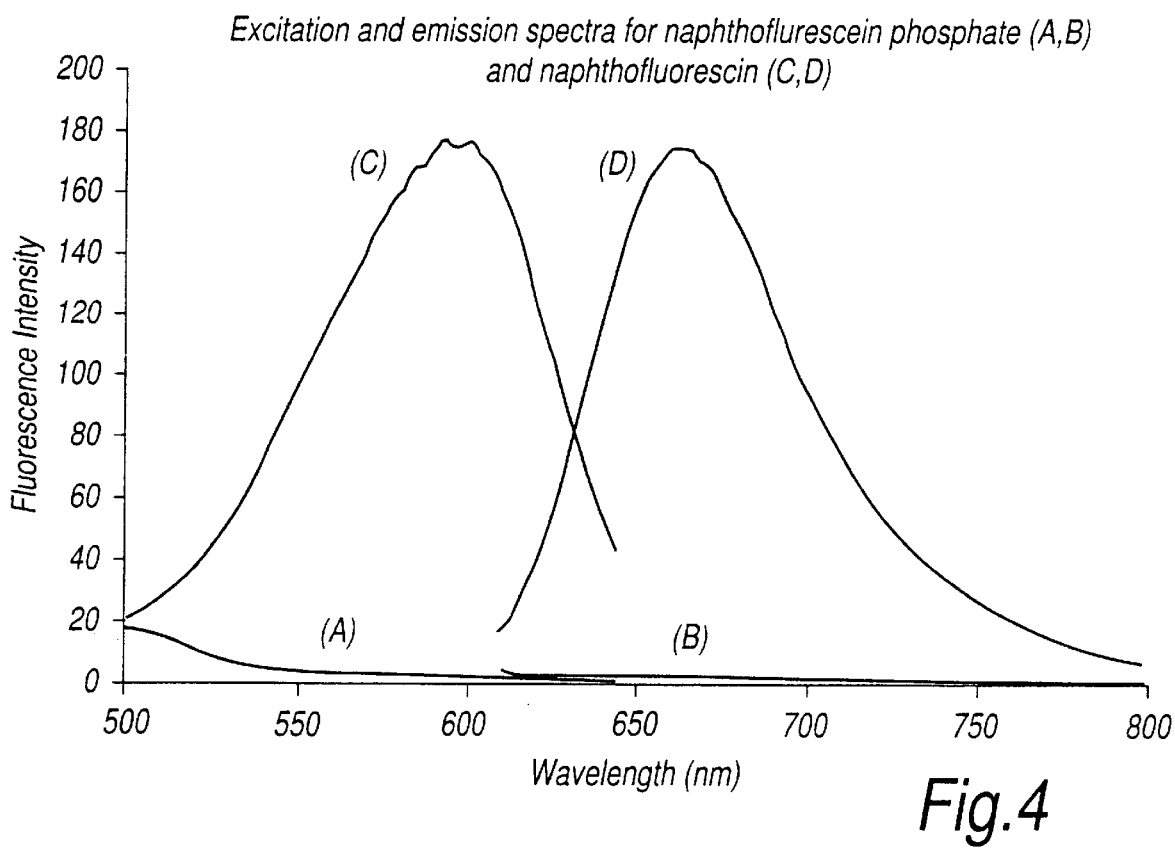
Fig.4 Excitation and emission spectra for naphthoflurescein phosphate (A,B) and naphthofluorescin (C,D)

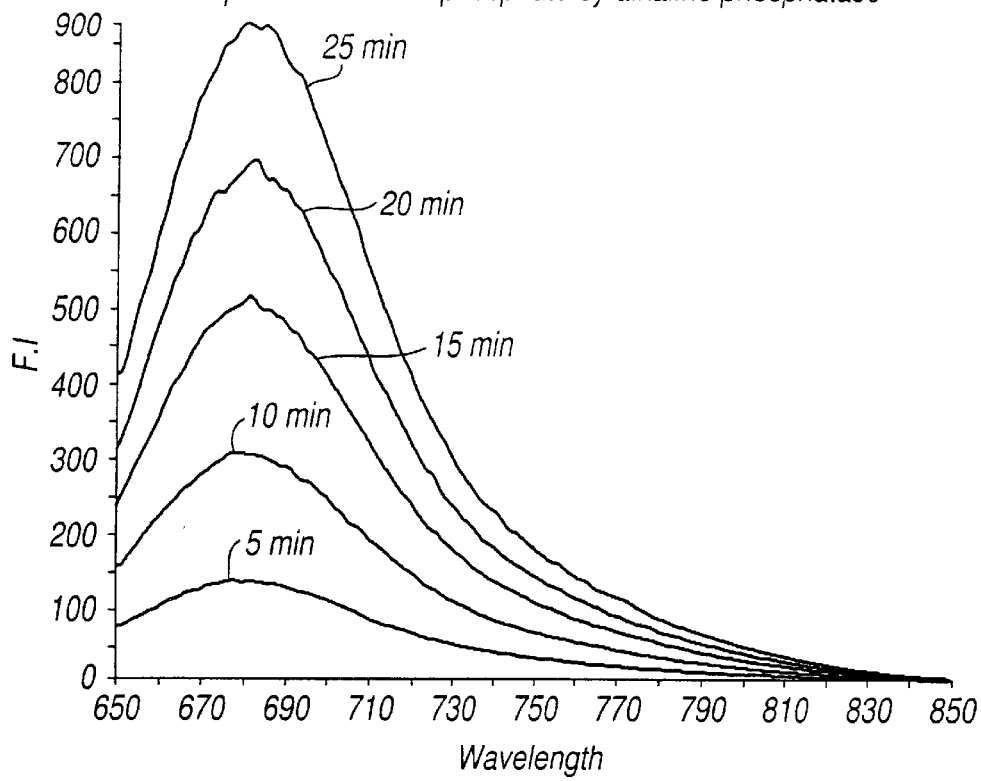
Fig.5 Influence of incubation time on production of naphthofluorescein from naphthofluorescein phosphate by alkaline phosphatase
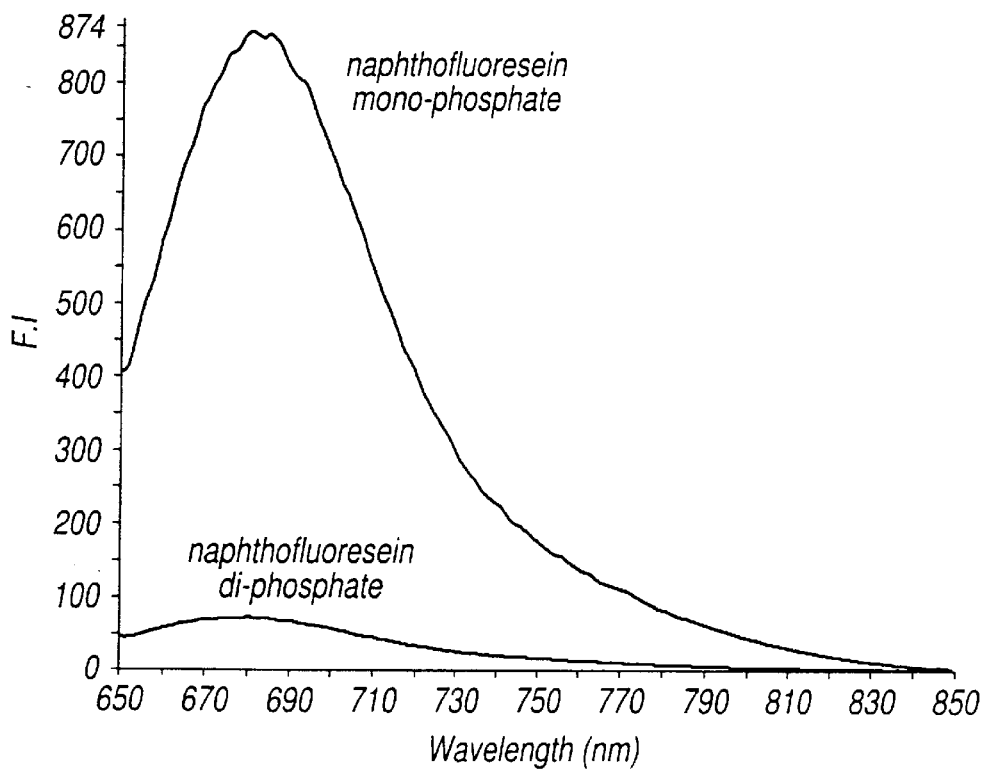
Fig.6 Comparison of production of naphthofluorescein from naphthofluorescein mono and di-phosphate by alkaline phosphatase after a 25 minute incubation at 22 C

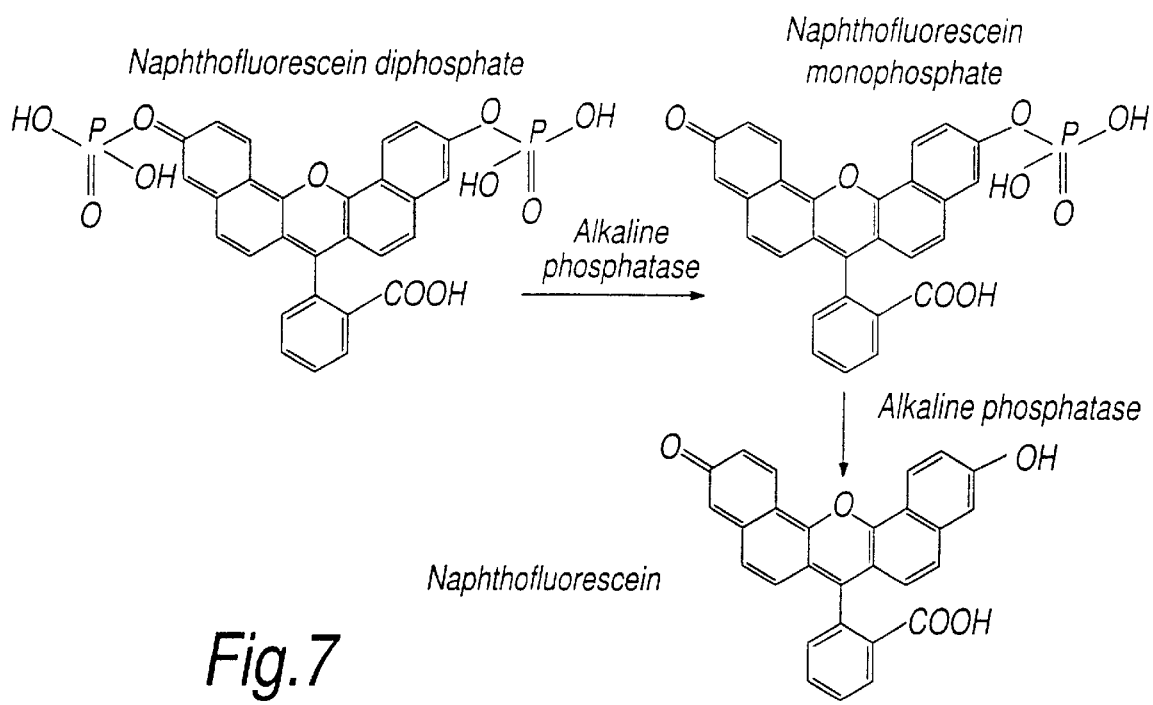
Fig.7
Structures for 4,10 dibromonaphthofluorescein and Vita blue
4, 10 dibromomnaphthofluorescein
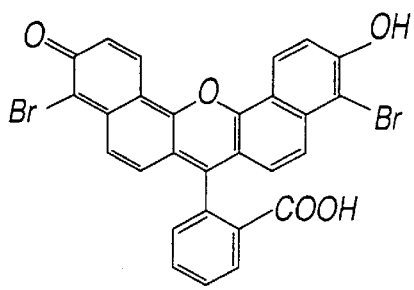
Vita blue
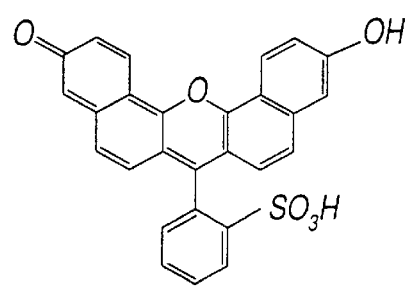
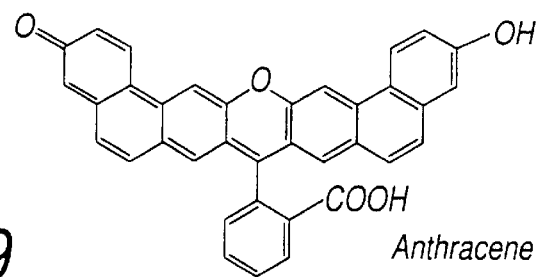
Anthracene derivative
Fig.9

Schematic diagram for multi target (enzyme/receptor) high throughput screening (HTS) using Kalibrant's core flow injection technology 1. Run buffer
2. Housing for potential drug(s)
3. Housing for target molecule e.g. enzyme or receptor
4. Mixing coil
5. Incubation loops
6. Separation device
7. Wash buffer
8. Flow cells
9. Detector

*Sequential Interval Pulse Generation by Laser Diode Driver*

Int = Intensity, t = time
System clock

Laser Pulse 1

Laser Pulse 2

Laser Pulse 3

Combination of Laser Pulses

Note: $\Delta t$ is the interval between $t1$ and $t2$ or $t2$ and $t3$ etc.

Fluorescence Pulse Generated from the
Flow Cell
System Clock

Laser Pulse 1

Fluorescence 1

Laser Pulse 2

Fluorescence 2

Laser Pulse 3

Fluorescence 3

Combination of Fluorescence Pulses
   Fluo Pulse 1  Fluo Pulse 2  Fluo

Data Acquisition

Note: $\Delta t_f = \Delta t$

COMPOSITION FOR USE IN FLUORESCENCE ASSAY SYSTEMS

PRIOR FOREIGN APPLICATIONS

This application is a 35 USC §371 filing of PCT/GB98/03750, filed Dec. 15, 1998, and claims priority from GB patent application number 9727355.1, filed Dec. 24, 1997.

1. Field of Invention

The present invention relates to a composition for use in fluorescence detection. The invention further pertains to a fluorescence assay method and uses of compositions in fluorescence assay methods.

2. Background of the Invention

Fluorescence measurements have been used increasingly for determination and analysis, especially in the biological field. For example, enzyme immunoassays (EIA) based on the determination of the enzyme as a marker has been extensively applied in the bioanalytical field [T. Portmann and S. T. Kiessig, J. Immunol. Methods (1992), 150, 5 and M. Oellerich, J. Clin. Chem. Clin. Biochem., (1989), 22, 895] owing to the high sensitivity and specificity of EIA, availability of many enzyme markers and long term stability of the label reagents and their operational safety. The most commonly used enzyme labels for EIA are alkaline phosphatase, horse radish peroxidase and galactosidase. Most enzyme labels are detected by spectrophotometry [H. Labrousse, J. L. Guesdon, J. Ragimbeau, S. Avrameas, J. Immunol. Methods (1982), 48, 133], spectrofluorimetry [E. Ishikawa, Clin. Biochem., (1987), 20, 375], chemiluminescence [H. Sasamoto, M. Maeda and A. Tsuji Anal. Chim. Acta (1995), 306, 161] and electrochemistry [K. P. Wehemeyer, H. B. Halsall and W. R. Halsall, Anal. Chem., (1995), 31, 1546].

Alkaline phosphatase has been widely used as a label in EIA and has been assayed spectrophotometrically using p-nitrophenyl phosphate (PNPP) [C. S. Chiang, T. Grove, M. Cooper et al., Clin. Chem. (1989), 35, 946], spectrofluorimetrically using 4-methyl umbelliferyl phosphate (4MUP), by chemiluminescence using adamantyl 1,2,-dioxetane aryl phosphate (AMPPD) and its derivatives [I. Bronstein, B. Edwards and J. C. Voyta, J. Biol. Chem., (1989), 4, 99], and electrochemically using phenyl phosphate [K. R. Wehemeyer, H. B. Halsall, W. R. Volle, and I. W. Chen, Anal. Chem., (1986), 58, 135] and p-aminophenyl phosphate (PAPP) [D. A. Palmer, T. E. Edmonds and N. J. Seare, Analyst, (1992), 117, 1679].

The known fluorimetric substrates of alkaline phosphatase are 4-methyl umbelliferyl phosphate and fluorescein diphosphate. These substrates (4-methyl umbelliferyl phosphate and fluorescein diphosphate) are hydrolysed by alkaline phosphatase to 4-methyl umbelliferone and fluorescein which fluoresce at circa 450 nm and 525 nm respectively. Naphthofluorescein phosphate (NFP) is an alternative to the above mentioned alkaline phosphatase substrates with numerous benefits. The product of NFP hydrolysis by alkaline phosphatase is naphthofluorescein which has spectroscopic characteristics of excitation 595 nm and emission 660 nm which clearly fall in the long wavelength/near infrared region of the electromagnetic spectrum. The benefits of working in the long wavelength region have been reviewed recently [J. N. Miller, Fluorescence spectroscopy, (1993), 5/2, 34]. These include
a) lower background scattering—Raman and Rayleigh
b) less photodecomposition
c) fewer bright fluorophores, hence less background fluorescence
d) availability of compact bright light sources
e) good solid state detectors.

It has recently been demonstrated by our research group that assays for or using alkaline phosphatase can be determined using a combination of naphthofluorescein phosphate, cyclodextrins or surfactant reagents and a solid state laser diode detector. Coinciding with the advances made in the fluorophores, has been corresponding advances in the detectors.

We have recently developed a detector apparatus which, inter alia, uses a fluorescence detector to analyse a sample in a fluid stream. One of the particular advantages of our new detector is its capability to analyse for more than one fluorophore in a single sample. This requires each fluorophore in the sample to be matched to a particular laser in the detector, i.e. the absorbance maximum substantially at the maximum wavelength of the excitation of a narrow bandwidth laser. There are a number of fluorophores which can be matched with commercially available lasers and the number of such fluorophores is constantly increasing.

SUMMARY OF THE INVENTION

The present invention seeks to provide new compositions for fluorescent detection.

According to a first aspect of the present invention there is provided a composition comprising an enzyme substrate which is a non-fluorescent derivative of a fluorophore, and a shifting reagent which shifts the absorbance wavelength maximum of the fluorophore which maximum is naturally above 450 nm, the shifting reagent being present in an amount predetermined to shift the maximum to a preset value.

The ability to control the absorbance maximum greatly increases the potential substrates when matching existing fluorophores to available light sources. The amount by which the maximum is shifted can be varied, normally by varying the amount of shifting reagent in the composition. In this way the analysis for samples containing a matched fluorophore is simplified compared to analysis with unmatched fluorophores as the spectrum is cleaner for the matched fluorophores.

Preferably, the fluorophore is selected from the group consisting of: xanthene dyes; polymethine cyanine dyes; phenoxazine dyes; thiazine dyes; phycobiliproteins; and mixtures thereof.

In many such cases the fluorophore is:
a) a xanthene dye selected from the group consisting of fluorescein, naphthofluorescein, and fluorescent derivatives of fluorescein and naphthofluorescein, other xanthene dyes and anthracene-based dyes;
b) a polymethine cyanine dye selected from the group consisting of Cy3, Cy5, Cy7 and indocyanine green;
c) a phenoxazine dye selected from the group consisting of nile blue, nile red and oxazine 750;
d) a thazine dye being methylene blue; and
e) mixtures thereof.

For example some preferred xanthene dyes such as Vita Blue and other fluorescent derivatives of fluorescein are described by Lee, L. et al. in Cytometry 10:151–164 (1989) and by Menchen, S. et al. in U.S. Pat. No. 5,188,934.

Normally, the amount of shifting reagent is less than 10% w/v in the appropriate solvent, e.g. a buffer and preferably the amount of shifting reagent is less than 5% w/v of the appropriate solvent.

Advantageously, the shifting reagent is selected from the group consisting of: cyclodextrins; substituted cyclodextrins; surfactants; detergents; -(3-[(3-cholamidopropyl) dimethylammonio]-1-propane sulphonate (CHAPS); -(3-[(3-cholamidopropyl)dimethylammonio]-2-hydroxy-1-propane sulphonate (CHAPSO); octyl β-glucoside; octyl β-thioglucopyranoside; sodium dodecyl sulphate (SDS); derivatives thereof; and mixtures thereof.

It is particularly preferred if the substrate is a phosphate derivative, and ester derivative, an imide derivative, an amide derivative or another derivative which is cleavable to the fluorophore.

For assaying for two unknowns in a sample, the composition further includes a second substrate comprising a non-fluorescent derivative of a second fluorophore, wherein the absorbance wavelength maximum of the second fluorophore in the presence of the shifting reagent is different from the maximum of the first fluorophore. The maximum of the second fluorophore may be shifted by the shifting reagent.

For assaying for a plurality of unknowns in a sample (multi-analyte determination), the composition comprises a plurality of substrates comprising a non-fluorescent derivative of a plurality of fluorophores, wherein each absorbance wavelength maximum of each respective fluorophore in the presence of the shifting reagent is different from the maximum of the other fluorophores. In which case the maximum of the some or each of respective fluorescent molecules may be shifted by the shifting reagent.

The composition will normally be used in an assay system and the assay system is advantageously selected from all types of assays using enzymes, for example selected from the group consisting of: immunoassays; enzyme immunoassays; enzyme-linked immunosorbent assays; and enzyme inhibition assays.

Preferably, the composition is supplied separately and the derivative of the first fluorophore, the other fluorophores if present and the shifting reagent are mixed together in the presence of the sample to be assayed or otherwise in the assay apparatus.

According to a second aspect of the present invention, there is provided a method of assaying for a desired product in a sample comprising the steps of:
a) combining the sample with a substrate and a shifting reagent, the substrate being a non-fluorescent derivative of a fluorophore and the shifting reagent is a reagent which shifts the absorbance wavelength maximum of the fluorophore;
b) using a light source to produce a fluorescent spectrum indicative of the desired product, wherein the light source has a maximum intensity at a known excitation wavelength and the shifting agent is used in an amount predetermined to shift the absorbance wavelength maximum to substantially coincide with the known excitation wavelength.

Normally the composition of the first aspect of the invention will be used as the shifting reagent and substrate in step a) of the method of the second aspect of the invention.

Advantageously, step a) comprises combining the sample with a plurality of enzyme substrates, each substrate being the non-fluorescent derivative of a fluorophore and each fluorophore having an absorbance wavelength maximum in the presence of the shifting agent different from the other fluorophore or fluorophores; and step b) comprises using a light source to produce a fluorescence spectrum indicative of the desired product, wherein the light source has maximum intensity at a plurality of known wavelengths which coincide with respective absorbance wavelength maximum of each fluorophore.

In a preferred embodiment, the method is for assaying a plurality of desired products.

The preferred light is a LED or a low power diode laser as this can provide an excitation beam with a narrow bandwidth so avoiding the need for filters and also utilising a lower power than light sources filtered to produce narrow bandwidths.

Preferably, a further desired product is also assayed in the sample, wherein a further enzyme substrate is combined in step a), the further substrate being a non-fluorescent derivative of a further fluorescent molecule.

According to a third aspect of the present invention there is provided the use of a reagent to shift the absorbance wavelength maximum of a fluorophore in a detection system. Advantageously, the agent comprises the shifting agent of as defined in the first aspect of the invention.

BRIEF DESCRIPTION OF THE DRAWINGS

The invention will now be described with reference to the accompanying drawings, in which:

FIG. 3 depicts the absorbance spectra of naphthoflourescein (A) and naphthoflourescein phosphate (B);

FIG. 4 depicts the excitation and emission spectra for [naphthofluorescein phosphate] (A—excitation) and (B—emission) and naphthofluorescein (C—excitation) and (D—emission);

FIG. 5 depicts the effect of time on alkaline phosphatase hydrolysis of naphthofluorescein phosphate;

FIG. 6 depicts a comparison production of naphthofluorescein from (A) and (B) of FIG. 2 by alkaline phosphatase at 22° C. after 25 minutes;

FIG. 7 depicts the alkaline phosphatase hydrolysis sequence of naphthofluorescein diphosphate and monophosphate;

FIG. 9 depicts three xanthene compounds;

DETAILED DESCRIPTION OF PREFERRED EMBODIMENTS

An embodiment of the present invention is illustrated hereinafter using napthofluorescein as the fluorescent molecule. Naphthofluorescein is demonstrative of the fluorescent xanthene dyes useful in the present invention. Examples of other xanthene fluorophores are 4,10-dibromonaphthofluorescein and vita blue (FIG. 9).

A particularly advantageous substrate of naphthofluorescein is the phosphate produced by replacing a hydroxide group on the outer benzene ring of naphthofluorescein as described hereinafter.

1) Synthesis of Naphthofluorescein Phosphate (NFP)

Figure 1:
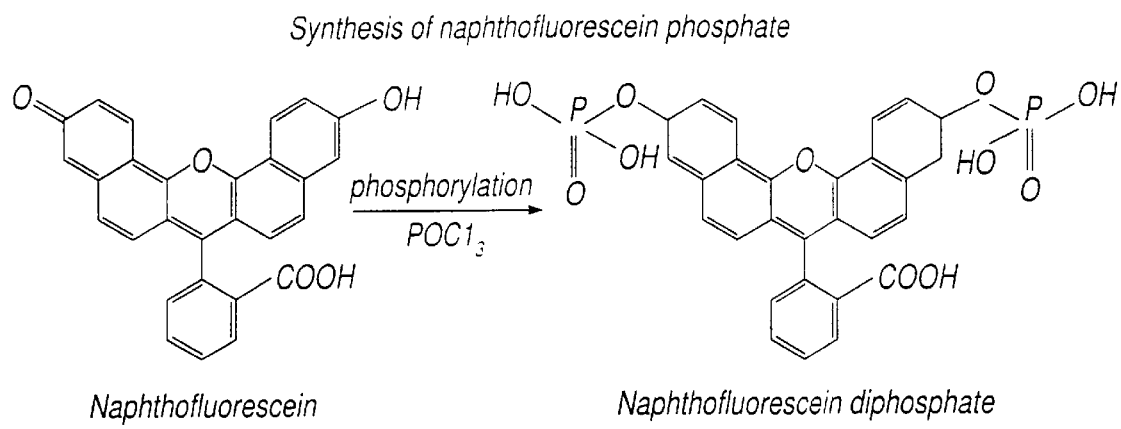
FIG. 1 depicts the synthesis of naphthofluorescein phosphate from naphthofluorescein.

The synthesis of naphthofluorescein phosphate was carried out according to the procedure described for fluorescein by Z. Huang, N. A. Olson, W. You and R. P. Haugland, J. Immunol. Methods (1992), 149, 261). The reaction step is shown in FIG. 1.

Method

To 0.25 mmol naphthofluorescein (0.1067 g) was added 4 ml dry pyridine under nitrogen gas at 0° C. To this solution was added 10.7 mmol phosphorous oxychloride (1 ml) in 4 ml dry pyridine under nitrogen gas at 0° C. The reaction mixture became complete within 30 minutes as shown by the steady spots in TLC (Rf=0.2 for NFP and Rf=0.8 for naphthofluorescein with 7:1:1:1 ethyl acetate:methanol:water:acetic acid). The reaction was quenched by pouring into 40 ml of cold water and neutralising with ammonium hydroxide to pH 7.0. Pyridine was then extracted with an excess of chloroform. The aqueous phase was lyophilised.

Figure 2:
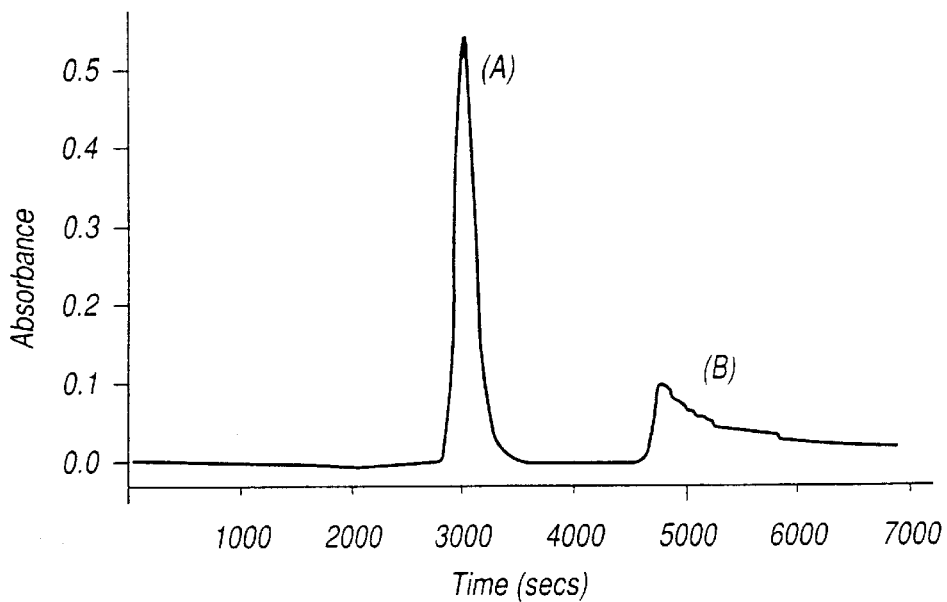
FIG. 2 depicts the purification profile of naphthofluorescein diphosphate (A) and monophosphate (B)

Naphthofluorescein phosphate was purified by size exclusion chromatography (SEC) using sephadex G-10 with a fractionation range of circa 100–700 [supplied by Pharmacia]. Two well resolved peaks were observed (FIG. 2) which are most likely naphthofluorescein monophosphate (NFMP) and naphthofluorescein diphosphate (NFDP). These peaks were collected and freeze dried. 250 mg of unpurified NFP yielded 69.2 mg of suspect NFMP and 89.1 mg of NFDP, i.e. total yield of 63.3%.

Characterisation of NFP a) Structural

Infra-red spectrum:
A strong absorption band occurred in the infra-red (KBr) at 1000–1500 cm-1 for phosphate which indicates a phosphate linkage and multiple phosphate bonds.

Mass spectrum:
The mass spectrum shows the parent ion at 593 region providing evidence that the conjugation was successful i.e. NFP had been produced.

b) Spectroscopic

UV-VIS absorption spectra:
Typically, NFP shows maximum absorbance before hydrolysis at approximately 500 nm whereas the absorbance after hydrolysis is maximal near 600 nm (FIG. 3).

Fluorescence spectra:
NFP, is a non-fluorescent substrate. On hydrolysis with alkaline phosphatase it exhibits fluorescence at 660 nm (when excited at 600 nm). FIG. 4 shows a typical excitation and emission profile of NFP and its hydrolysis product naphthofluorescein.

c) Comparative enzymatic studies of NFP, NFMP, NFDP and 4MUP (a conventional alkaline phosphatase fluorogenic substrate for illustrative purposes).

FIG. 5 shows the effect of incubation time on the alkaline phosphatase hydrolysis of naphthoflourescein phosphate for naphthoflourescein. The kinetic parameters of NFMP and NFDP the purified components of NFP were assessed and compared with equivalent characteristics of 4MUP a conventional fluorogenic substrate for alkaline phosphatase.

Figure 8:
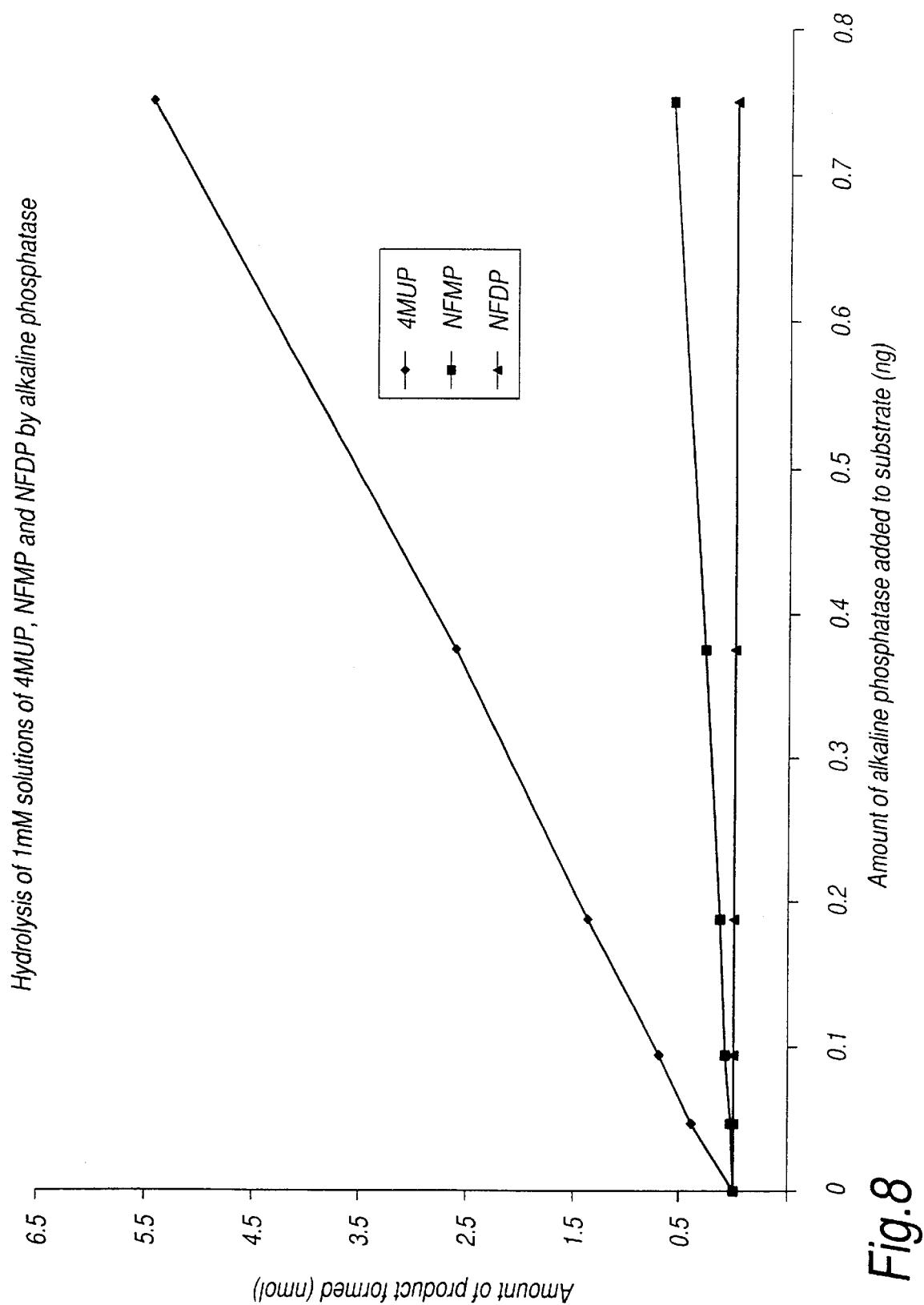
FIG. 8 illustrates the efficiency of three alkaline phosphatase substrates.

NFMP was found to be a more efficient substrate for alkaline phosphatase than NFDP (FIG. 6). A possible reason for this finding is that NFDP hydrolysis occurs via NFMP, therefore a longer period of time is required to completely hydrolyse all the NFDP to naphthofluorescein (i.e. hydrolysis is a two stage process) which is illustrated in FIG. 7. Of the three substrates investigated 4MUP was found to be a better substrate than NFMP or NFDP (FIG. 8) for alkaline phosphatase. 4MUP has a superior initial reaction velocity than NFMP and NFDP. The amount of product formed per ng alkaline phosphatase per min for 4MUP, NFMP and NFDP were 0.36, 0.038 and N/A respectively.

The Michaelis Menten constant (Km) (which is an indication of the efficiency of a substrate for an enzyme) was determined for the above named substrates. The smaller the Km value of a substrate the more efficient it is as a substrate. The Km for 4MUP, NFMP and NFDP was found to be 0.092, 0.22 mM and N/A respectively. Although the enzyme kinetics of 4MUP appear to be superior than that of NFMP and NFDP, NFMP is suitable for use as a substrate in enzyme assays. NFDP on the other hand suffers from the fact that its hydrolysis involves 2 steps (FIG. 7).

Other xanthene fluorophores can be similarly phosphorylated. For example are 4,10-dibromonaphthofluorescein, vita blue and the anthracene derivative shown in FIG. 9 could be phosphorylated to form non-fluorescent compounds (substrates) which would be fluorescent after hydrolysis by alkaline phosphatase. The anthracene derivative is prepared in a similar manner as shown in FIG. 1 and similarly to 4,10-dibromonaphthofluorescein and vita blue. The anthracene derivative will normally be derivatised or otherwise to make it more soluble in aqueous media by routine techniques.

Shifting Reagents

Investigations into the effects of cyclodextrins, detergents and surfactants on the fluorescence intensity of some xanthene-based fluorophores (naphthofluorescein and dibromonaphthofluorescein) led to the observation that the absorbance wavelengths of these compounds were shifted further to the red end of the electromagnetic spectrum in the presence of some cyclodextrins and surfactants.

It has been found that useful shifting agents include: cyclodextrins; substituted cyclodextrins; surfactants; detergents; -(3-[(3-cholamidopropyl) dimethylammonio]-1- propane sulphonate (CHAPS); -(3-[(3-cholamidopropyl) dimethylanmonio]-2-hydroxy-1-propane sulphonate (CHAPSO); octyl β-glucoside; octyl β-thioglucopyranoside; sodium dodecyl sulphate (SDS); derivatives thereof.

Figure 10:
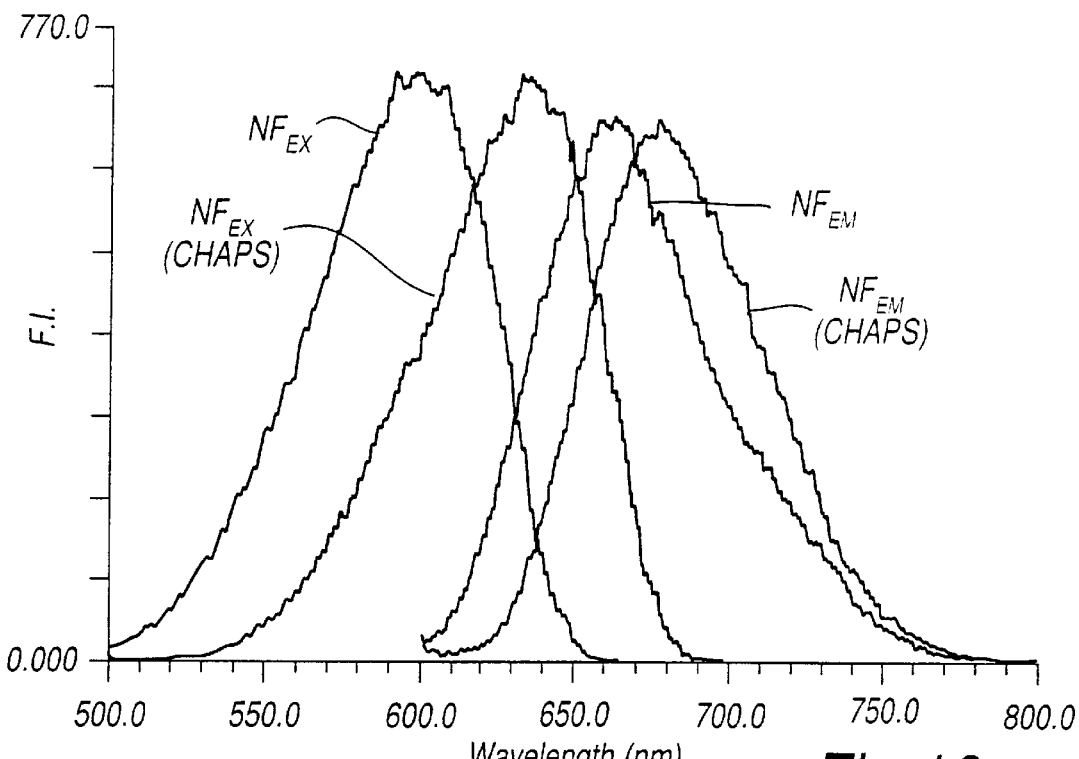
FIG. 10 depicts the excitation and emission spectra of naphthofluorescein with and without a shifting reagent (CHAPS 3% w/v)

Using a range of cyclodextrins, surfactants and detergents at different concentrations it was found that absorbance and emission wavelength shifts of between 4 and 46 nm were observed for the xanthene fluorophores as shown in tables 1 and 2 and FIG. 10. (0.1 MNaoH representing the control).

Figure 21:
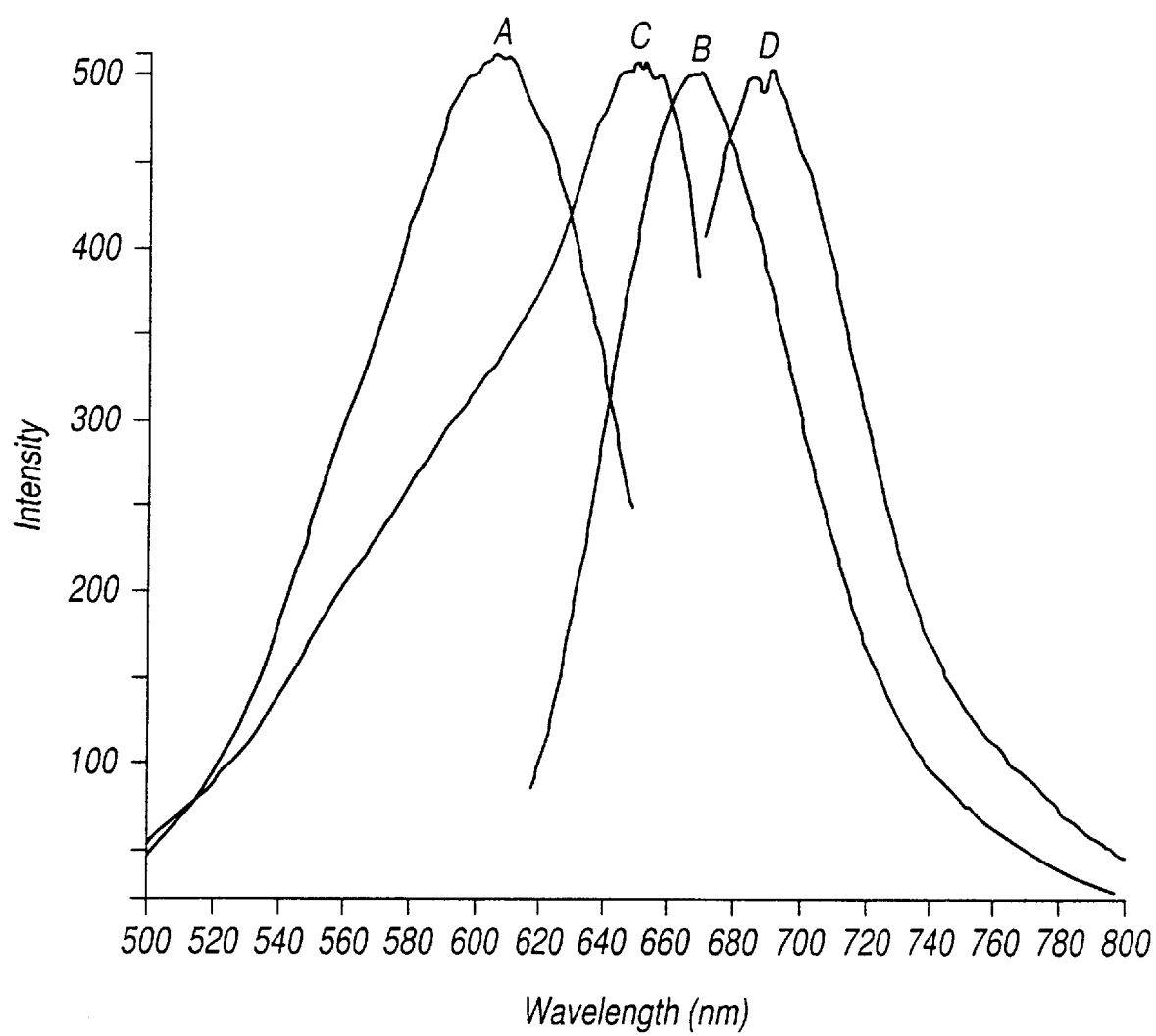
FIG. 21 depicts excitation and emission spectra of naphthofluorescein succinimidyl ester (NFSE) (A—excitation, B—emission) and NFSE conjugated to Albumin (C—excitation, D—emission)
Figure 22:
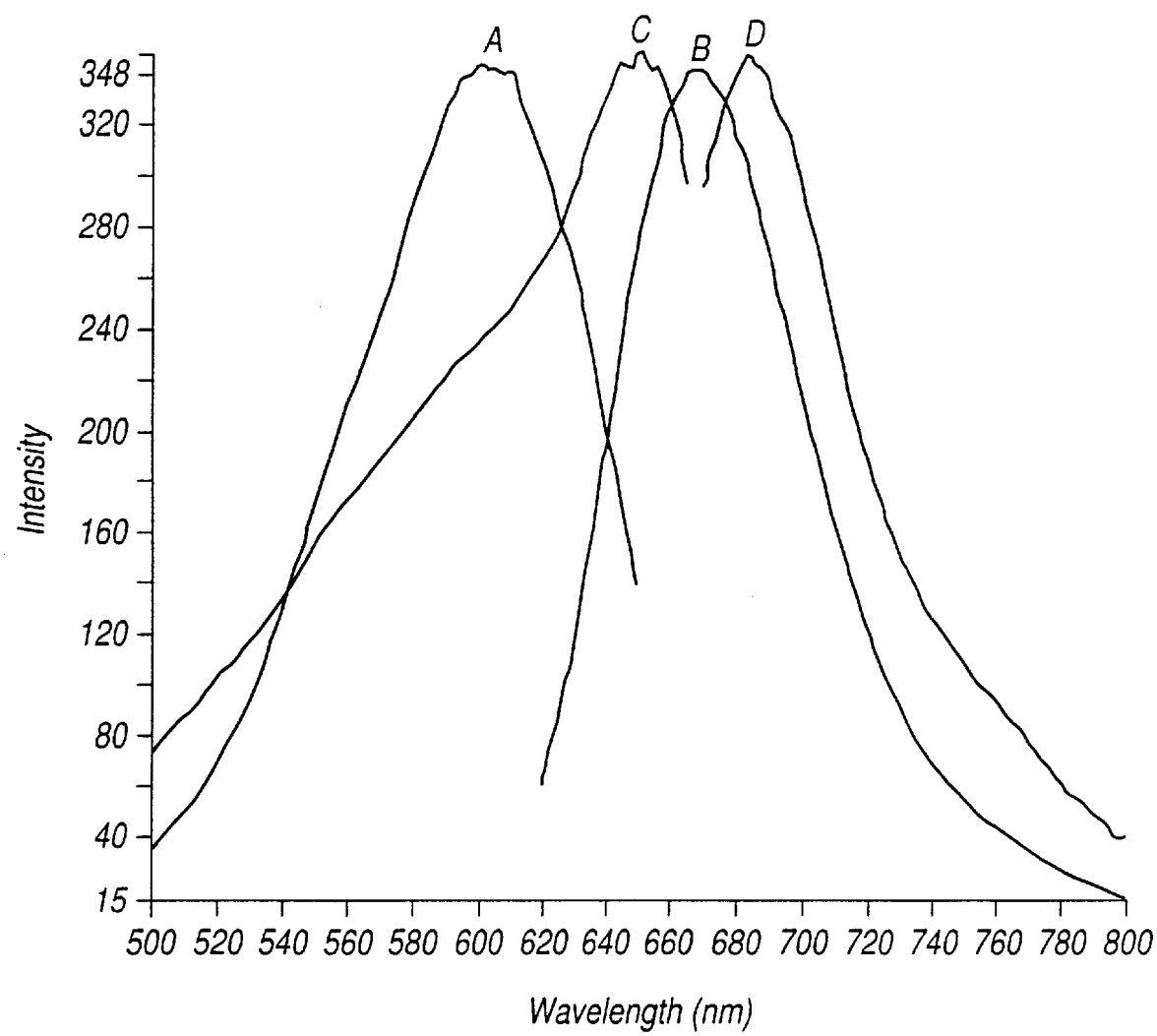
FIG. 22 depicts excitation and emission spectra of naphthofluorescein succinimidyl ester (NFSE) (A—excitation, B—emission) and NFSE conjugated to α-Casein (C—excitation, D—emission)
Figure 23:
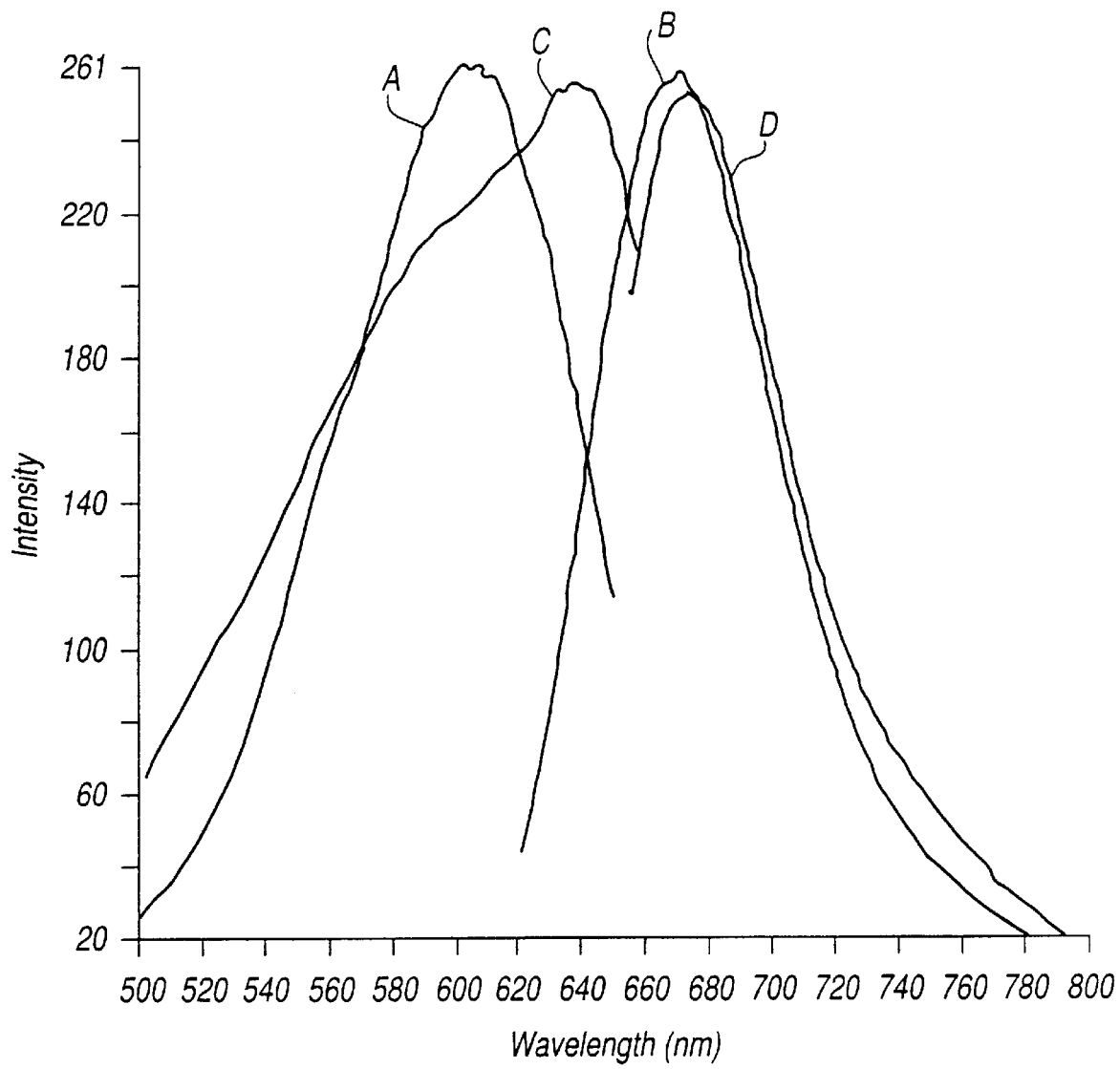
FIG. 23 depicts excitation and emission spectra of naphthofluorescein succinimidyl ester (NFSE) (A—excitation, B—emission) and NFSE conjugated to Ovalbumin (C—excitation, D—emission)
Figure 24:
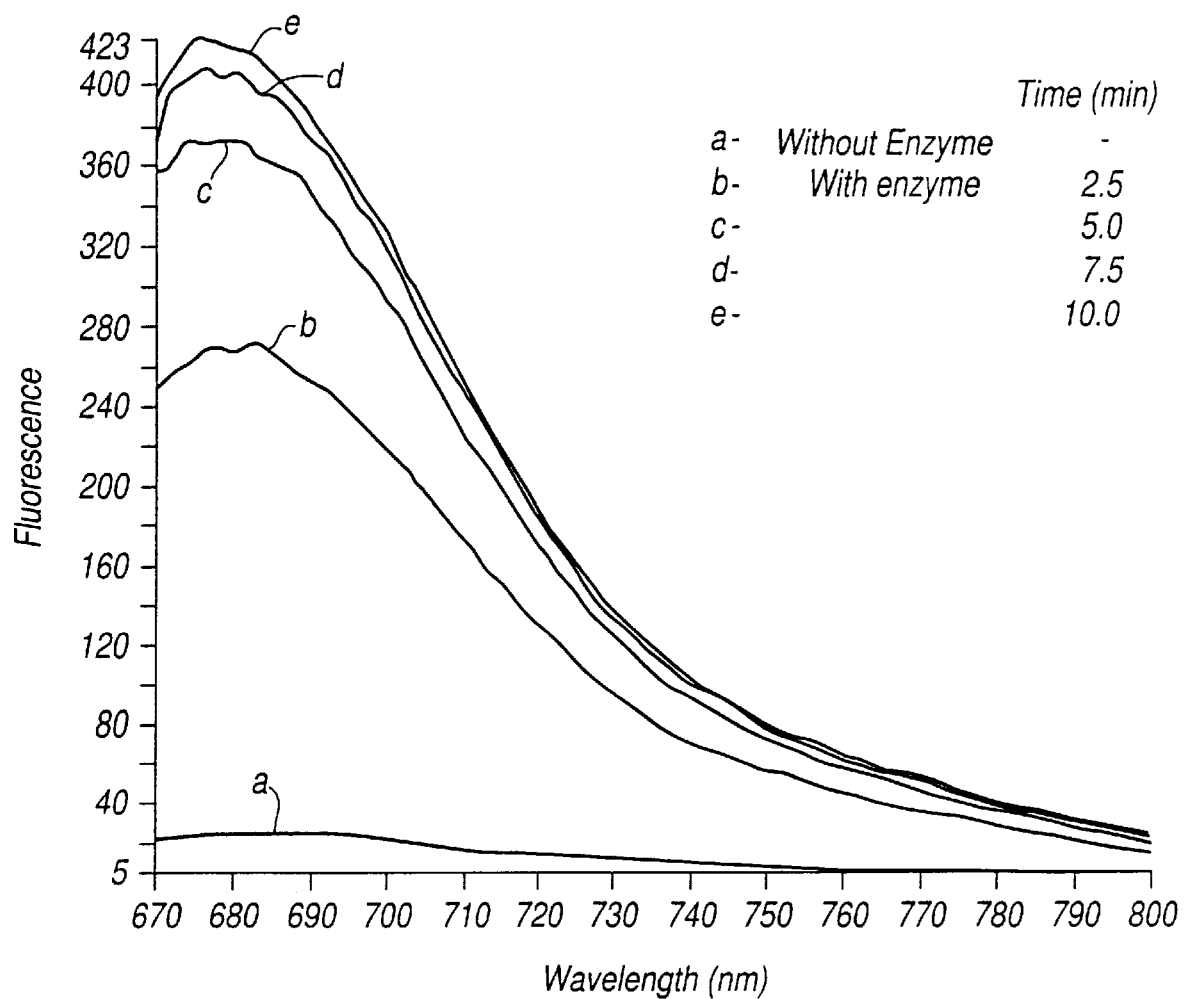
FIG. 24 illustrates effect of incubation time on naphthofluorescein-albumin conjugate hydrolysis to naphthofluorescein succinimide by alkaline protease.
Figure 25:
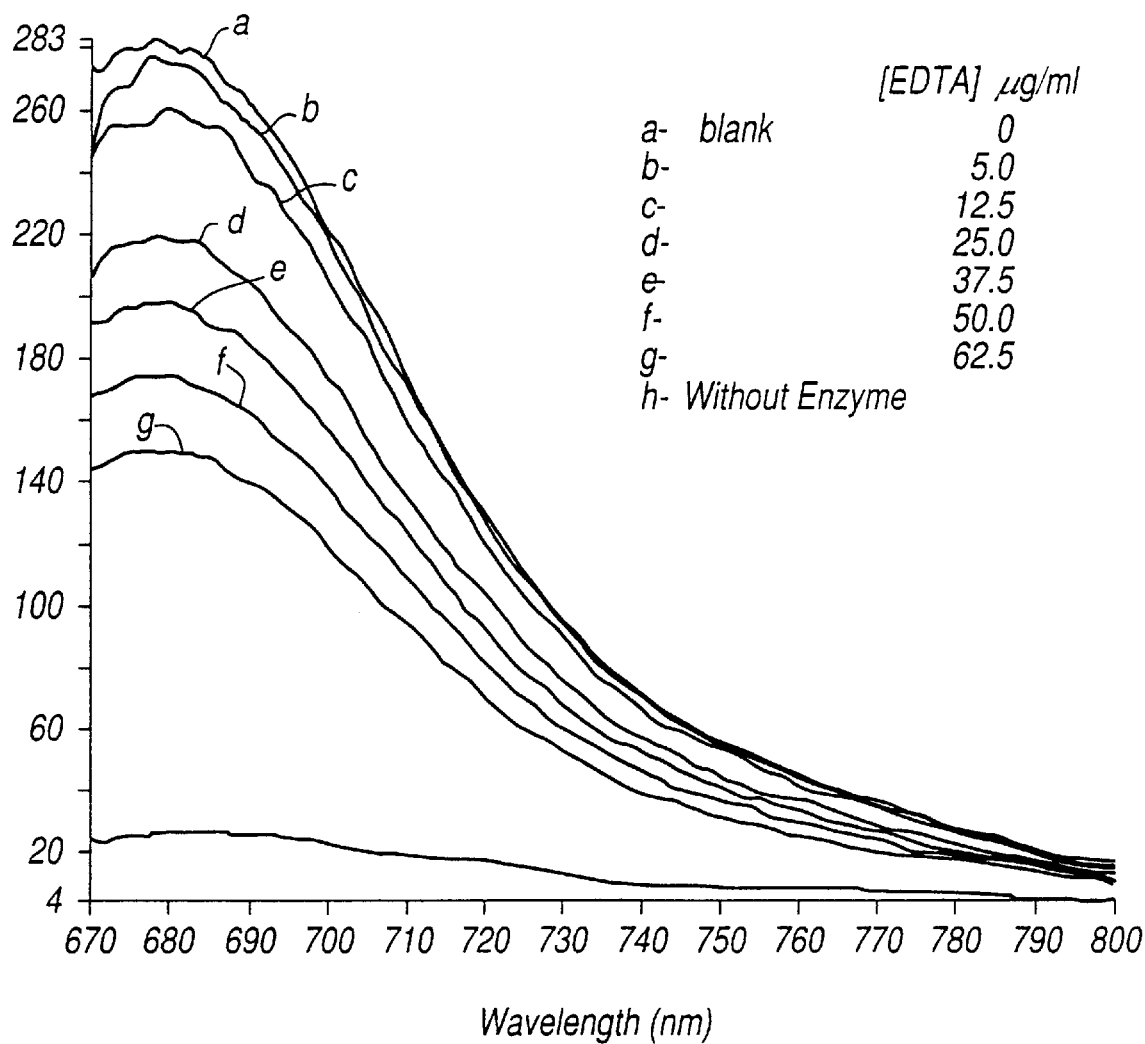
FIG. 25 illustrates effect of EDTA on the hydrolysis of naphthofluorescein-albumin conjugate to naphthofluorescin succinimide by alkaline protease (10 minutes incubation at 37° C.).

The conjugation of naphthofluorescein succinimidyl ester (NFSE) to albumin, ovalbumin and α-Casein resulted in a shift of the absorbance, excitation and emission wavelengths of naphthofluorescein further to the red end of the electromagnetic spectrum. Naphthofluorescein normally has an absorbance and excitation wavelength maxima of 600 nm and an emission maxima wavelength of 660 nm. The shift in absorbance, excitation and emission wavelengths for the albumin, ovalbumin and α-Casein conjugated to naphthofluorescein are given in table 3 and are shown in FIGS. 21–23. This red shift phenomenon is similar to that observed using cyclodextrins, detergents and surfactants with naphthofluorescein. Over labelling of the naphthofluorescein protein conjugates resulted in the quenching of the naphthofluorescein fluorescence. Treatment of the conjugates with specific enzymes resulted in the regeneration of the naphthofluorescein conjugate fluorescence as a result of the cleaving of the protein into smaller naphthofluorescein peptide fragments. Heavily labelled naphthofluorescein conjugates of albumin, ovalbumin and α-Casein (with initial ratios of dye to protein of 50:1 and 100:1) were then used in the development of a HTS screening assay.

Results

TABLE 1

Absorbance wavelength shift of Naphthofluorescein and 4,10 Dibromonaphthofluroescein

| Cyclodextrin/surfactant Concentration (% w/v) | Naphthofluorescein Absorbance maximum(nm) | Dibromo- napthofluorescein Absorbance (nm) |
| --- | --- | --- |
| In 0.1M NaoH | 595 | 610 |
| α-cyclodextrin (5%) | 596 | 611 |
| β-cyclodextrin (5%) | 603 | 626 |
| γ-cyclodextrin (5%) | 599 | 621 |
| 2 Hydroxy propyl β-cyclodextrin (5%) | 616 | 635 |
| Methyl β-cyclodextrin (5%) | 609 | 633 |
| CHAPS (5%) | 630 | 656 |

TABLE 2

Absorbance and emission wavelength shift of Naphthofluorescein

| Concentration CHAPS (% w/v) | Absorbance maximum(nm) | Emission maximum(nm) |
| --- | --- | --- |
| 0 | 595 | 660 |
| 0.16 | 599 | 665 |
| 0.33 | 604 | 665 |
| 0.625 | 617 | 670 |
| 1.25 | 627 | 675 |
| 2.5 | 630 | 675 |
| 5.0 | 630 | 680 |
| 10 | 635 | 680 |

TABLE 3

Absorbance and emission wavelength shift of Naphthofluorescein protein conjugates

| Conjugate | Absorbance/excitation maxima(nm) | Emission maxima (nm) |
| --- | --- | --- |
| Naphthofluorescein-albumin | 640 | 685 |
| Naphthofluorescein-ovalbumin | 636 | 675 |
| Naphthofluorescein-α-Casein | 650 | 685 |

Figure 11:
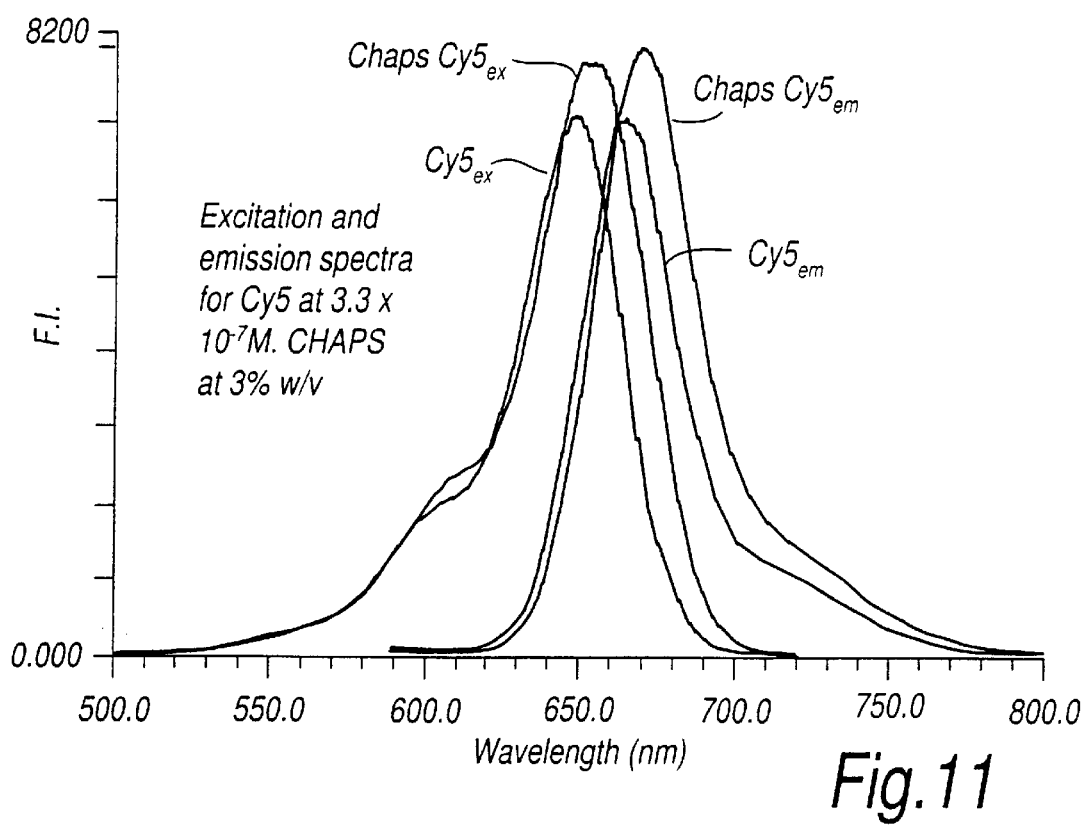
FIG. 11 depicts the excitation and emission spectra of Cy5 with and without a shifting reagent (CHAPS 3% w/v)

CHAPS was also found to enhance the fluorescence intensity of Cy5 (a cyanine based fluorophore with spectral characteristics of 648 nm excitation and 670 nm emission) by a factor of about 10. A slight wavelength shift was observed circa 5 nm for the absorbance/excitation profile 649 nm to 654 nm and circa 7 nm for the emission profile 664 nm to 671 nm (FIG. 11).

The ability of CHAPS, cyclodextrin and other similar compounds to shift the absorbance maximum of naphthofluorescein and similar compounds provides a means to match the maximum with the output of a narrow bandwidth laser so as to provide very clean spectrum for analysis. Such matched fluorophores are particularly suitable for use with the detector apparatus described in GB Application Patent No. 9717021.1 for a multi-analyte fluorescent detector filed on Aug. 12, 1997, the content of which are herein incorporated by reference and described briefly hereinafter. However, the composition of the present invention is useful in any fluorescent detector which is assaying for the presence of a particular species.

Preferred Detector Apparatus

Figure 17:
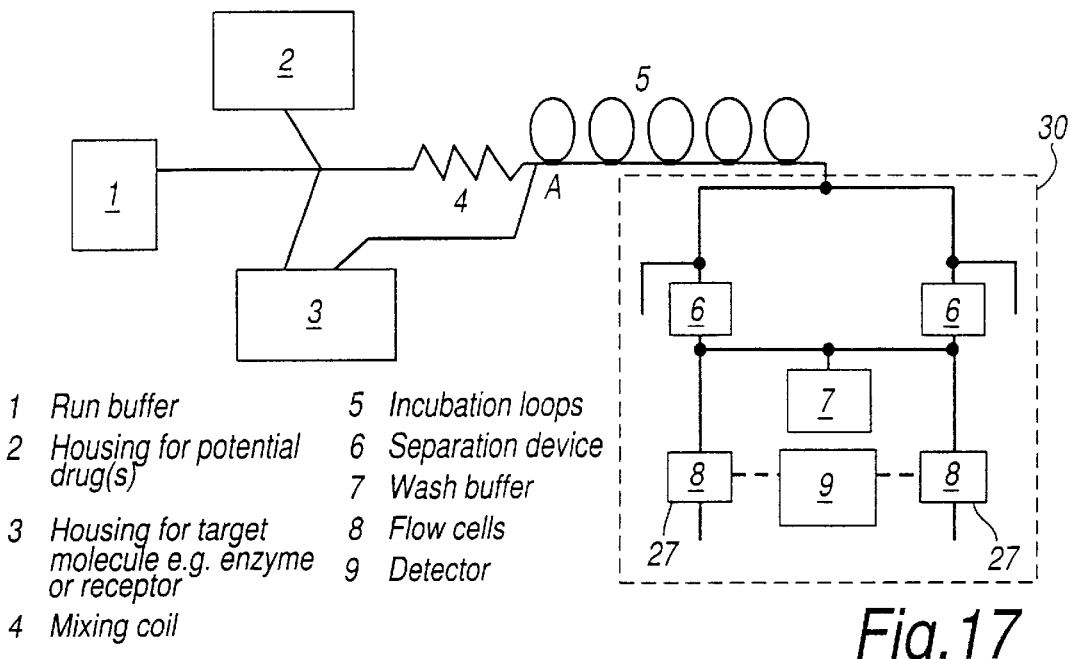
FIG. 17 depicts a flow injection apparatus.
Figure 18:
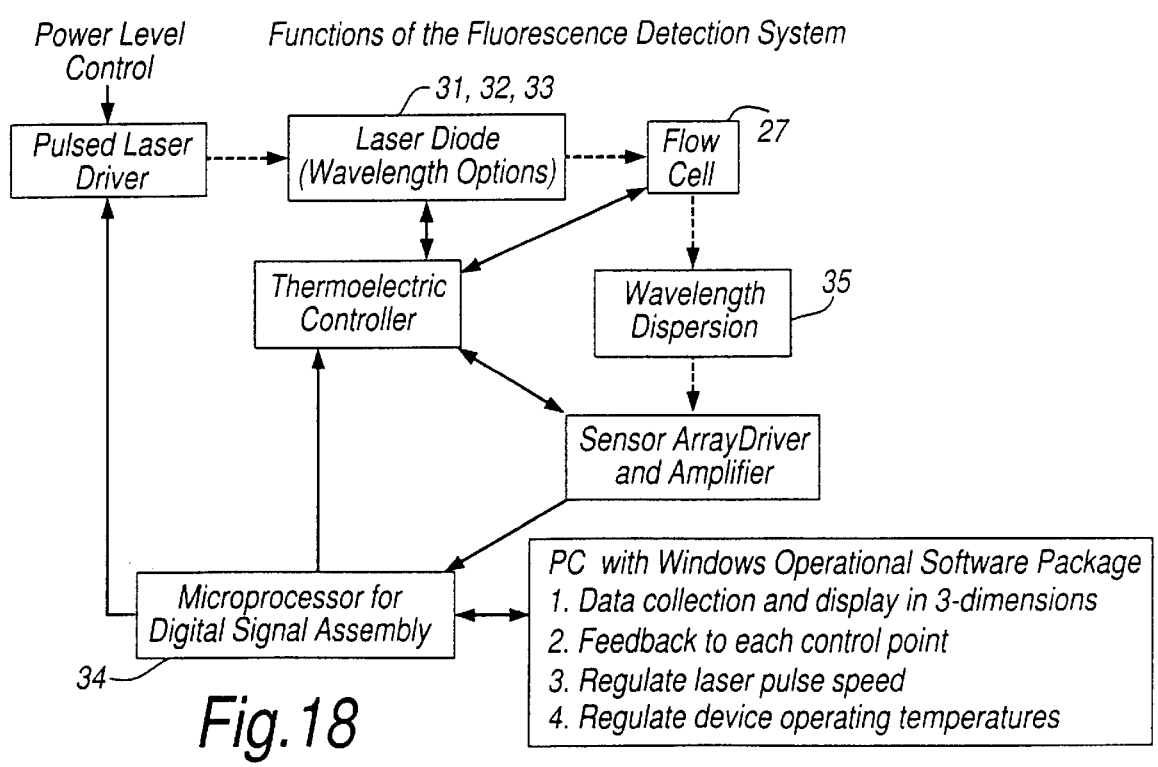
FIG. 18 depicts an enlarged version of the detector shown in FIG. 17.
Figure 19A:
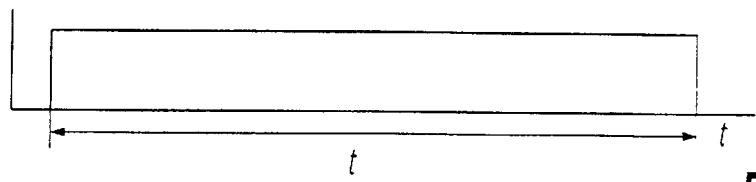
FIG. 19 illustrates a sequential time control of the lasers of the apparatus of FIGS. 17 and 18.
Figure 19B:
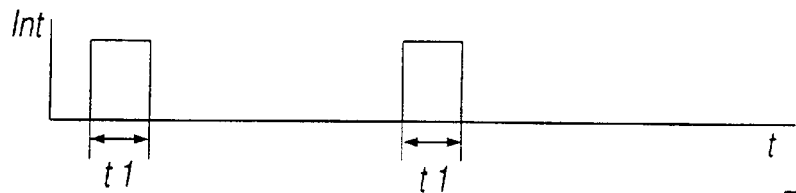
Figure 19C:
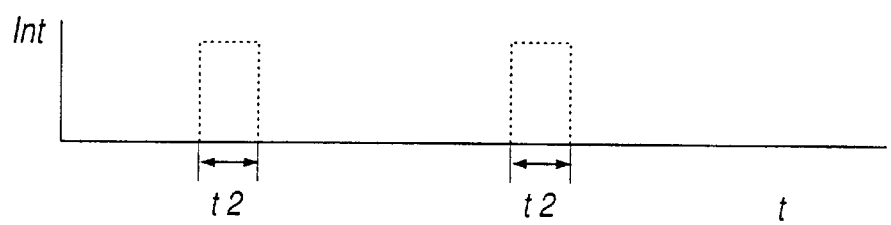
Figure 19D:
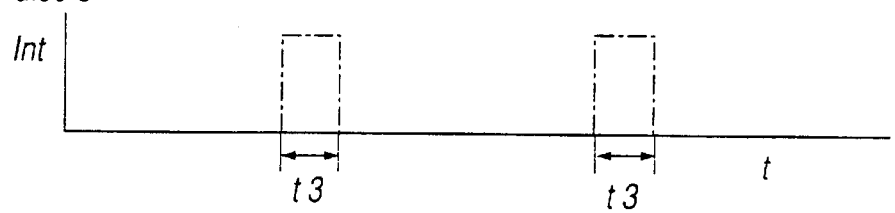
Figure 19E:
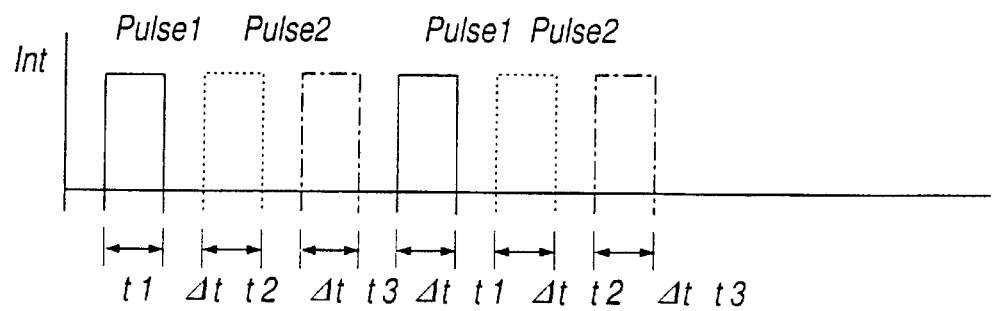

FIG. 17 illustrates the main units of a preferred embodiment of the multiple analyte detector 30 in a flow injection system of WO 97/29376. As shown in FIG. 18 a control unit 34 is linked to a user interface via a personal computer or other device. The linkage will normally take the form of a software interface. The software interface will receive from the user or from upstream of the detector 30 the information on the interval between samples and/or the tests being performed on each of the samples. The control unit operates the components of the detector 30 in accordance with the received information as described in more detail hereinafter.

In some circumstances the qualitative measurement may be simply whether or not the target substance was detected i.e. was any or more than a certain amount of fluorescence attributable to the fluorophore present. Often however a more precise measurement of the amount of target substance will be required.

1. Use of Two or More Excitation Wavelengths

The system provides two or more wavelength options, preferably provided by laser diodes 31. A laser diode has several benefits when compared with a conventional excitation source including:

a. No requirement for a high power supply and small power consumption
b. Fixed wavelength and constant light output
c. Compact unit with digital control
d. Easy replacement for wavelength options.

In this detection system two or more laser diodes 31, 32, 33 (or other light source) are employed as the excitation source each of which is controlled by a laser driver to produce sequential interval pulses of light as shown in FIG. 19. Of course only one laser may be necessary for some embodiments for example where only single analytes are assayed. The lasers are arranged to shine on a test cell 27 where fluorescent molecules (fluorophores) may be present and the resulting fluorescence emission is guided to the sensor array 35. These fluorophores are chosen because they have spectral properties, which match those for a specific laser and each laser 31, 32, 33 has at least one specific and separate fluorophore partner. In this matching process the present invention is particularly advantageous.

The pulse rate can be calculated and controlled through a programmable microprocessor or the control software so that the laser driver speed and the interval time of the pulses match the requirements of the sensor array so as to capture the fluorescence from each fluorophore into the appropriate data channel. The lasers may be operated sequentially or one laser may be operated (pulsed) repeatedly before another laser is operated.

2. Multichannel Time Gating Approach

The use of a pulsed laser source means that the sensor array 35 receives a pulsed light signal from the flow cell 27 that consists of the fluorescence from the fluorophores in the flow cell 27, non specific fluorescence from any other molecules present and any scattered light from the laser source. In traditional fluorimeters the non-specific or background fluorescence, along with the scattered light, is removed or greatly reduced by the use of filters or monochromators. The fluorimeter described here can make specific fluorescence measurements without the need of filters or monochromators.

It is well known that one of the major advantages of measuring fluorescence in the near infra red (NIR) region (approximately over the range 600–900 nm) is that there are relatively few endogenous NIR fluorescent molecules. Therefore background interference from non-specific endogenous fluorescence is greatly reduced. Scattered light from the broad band excitation source in traditional fluorimeters is often a problem because to obtain maximum detection sensitivity it is necessary to use a wide band pass setting, often up to 20 nm. This ensures the maximum amount of light falls on the sample being analysed but at the expense of much increased Rayleigh scatter, which can often swamp the specific fluorescent signal. With a laser diode source it is possible to deliver a large amount of light power in a very tight bandwidth (2–4 nm) thereby minimising the influence of Rayleigh scatter to a short spectral range. Furthermore the intensity of this scatter signal varies with the inverse of the wavelength to the fourth power and so operation in the NIR region greatly diminishes the magnitude of the scattered light. In spite of the advantages of working in the NIR region some non specific signal will still be detected at the sensor, including that from co-excitation of some of the other fluorophores and so a multi channel time gating (MCTG) approach is used with the sensor array to select out the fluorescence of interest. With MCTG the fluorescent signal from each laser pulse is collected from the sensor 35 and stored in a data channel specific for that laser 31. In this way two or more emission pulses can be monitored from two or more fluorophores in the test cell by the use of two or more laser diodes if this is desired. Each laser diode 31, 32, 33 pulses in turn to sequentially excite the fluorophore with matched spectral properties. Each laser pulse has its own specific interval time and this is shared by the associated emission pulse. It is therefore possible to time gate the emission pulse generated by a specific laser into a selected channel for data acquisition and feedback the data to regulate the sensor array.

Figure 20A:
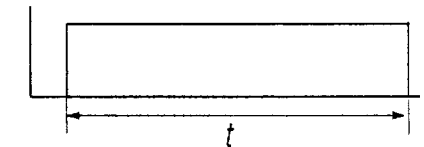
FIG. 20 illustrates data acquisition of fluorescence emissions of FIG. 19.
Figure 20B:
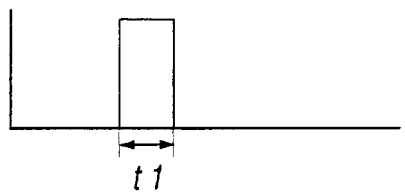
Figure 20C:
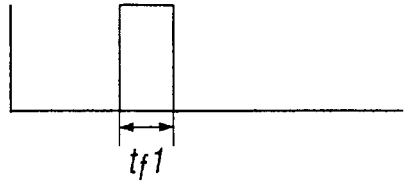
Figure 20D:
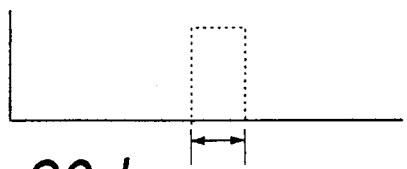
Figure 20E:
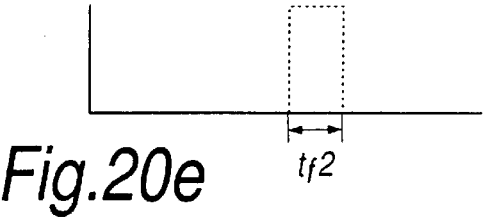
Figure 20F:
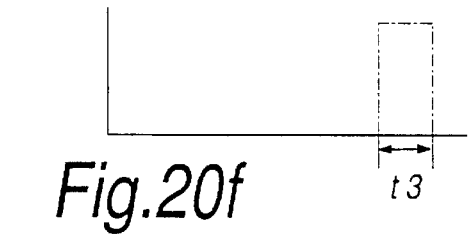
Figure 20G:
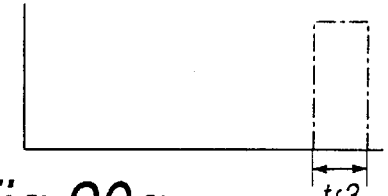
Figure 20H:
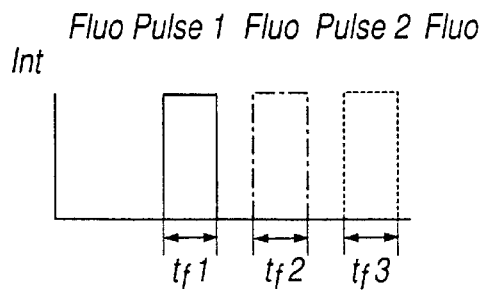
Figure 20I:
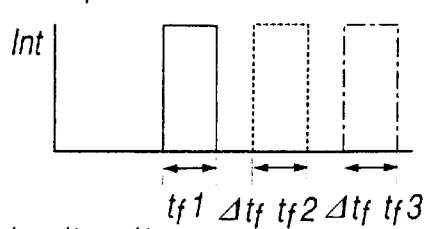

In this way fluorescence measurements can be made as follows. The overall timing of all events is controlled by the system clock (FIG. 20a), at a given time frequency laser 1 fires a light pulse of defined time and intensity (FIG. 20b). Fluorophore 1 responds with fluorescence over a similar time period and at an intensity dependent on its concentration (FIG. 20c). The other laser/fluorophore pairs operate in sequence in a similar fashion (FIGS. 20d–20h) and the emission pulses are collected from the sensor into their respective data channels (FIG. 20i). In order to minimise the influence of variable fluorescence decay the data collection ceases fractionally before the laser pulse finishes.

In addition to using the lasers in sequential pulsed mode it is possible to drive them in constant wave mode, where each laser operates continuously and illuminates the sample for the whole time it is being measured. If two or more lasers are operated in this way and paired with suitable fluorophores so that there is a recognisable fluorescent response for each laser source then multiple analyte measurements can be made. The use of the detector will produce a spectrum where, for example the excitation of three fluorophores where peak 1, peak 2 and peak 3 are the fluorophores emission after excitation by the fixed wavelength lasers 1, 2 and 3 respectively. The scattered laser light has been omitted for clarity. The mixed emission signal can now be dealt with in two ways, firstly as described below in the evaluation of pulsed emission signals, where multivariate analysis software can be used to generate the pure emission spectra. Alternatively the sensor can be programmed to collect data over a narrow wavelength range specific for each label i.e. $\Delta\lambda_1$, $\Delta\lambda_2$, and $\Delta\lambda_3$, thereby avoiding the scattered light and the intensity of each peak indicates the strength of fluorescence in the solution which can then be used as a quantitive measure.

Use of constant wave lasers and two dimensional CCD detectors and spectrographs to collect the fluorescence spectra from two or more laser diodes can provide an alternative to pulsing the laser. Time gating the detection, i.e. spectral separation, could be achieved spatially at the input of the spectrograph using optical fibre coupling of the fluorescence signals taken from different parts of the flow cell. Liquid light guides offer an alternative approach to coupling because of their much higher throughput compared to bundles.

Although it is preferred to use separate light sources, it is possible to use filters designed to allow passage only to the wavelengths of the emissions from the desired fluorophores. A variable wavelength filter can be used to modify the excitation light, and this can also be used on the emitted fluorescence. However, filters, variable or fixed, are not preferred as more energy is used to cause the same degree of signal compared to the separate light sources.

3. Wavelength Dispersion onto the Sensor Array Device for Data Acquisition

The fluorescence emission from the flow cell is over a wide spectral range and so a device is required to disperse this spectrum over the sensor array. A preferred option is where the emitted pulse of fluorescence is focused onto a polychromator and then dispersed across the sensor array 35 to reveal the emission spectrum. Alternatively a monochromator is used to rapidly scan the emission beam in order to generate the emission spectrum at the sensor. Because the spectral properties of each fluorophore is known a pure reference sample is first used to wavelength calibrate the sensor array for each laser/fluorophore pair and the spectral data stored in the relevant data channel in the computer. When sample measurements are taken the emission profile gathered in the data channel can be examined against the expected profile and multivariate analysis software used to remove the non-specific components, including that of spectral overlap from co-excited fluorophores. The sensor array 35 can be programmed to collect data over a narrow wavelength range specific for each label and the intensity of each signal indicates the strength of fluorescence in the solution, which can then be used as a quantitative measure.

For this application it is preferred to use a highly sensitive and fast speed sensor to capture the fluorescence from the solution in the flow cell. A suitable sensor would be a CCD photo-electric device which operates in a rapid self scan mode so that there is quantitative capture of the emission photons with excellent signal to noise characteristics, due mainly to very low dark current in the device. The CCD has its own driver assembly through which the scan time can be set to match the speed of the emission pulse. The control means includes a programmable microprocessor and an interface digitally control the data acquisition from the sensor array.

Alternatively, it would be possible to use a tunable filter, such as an acousto-optic tunable filter, as the wavelength selection element in place of a spectrograph. A single detector element such as a photomultiplier tube or photo detector could replace the CCD array. In this case it would be normal for the light source to pulse and fluorescence spectra to be accumulated in sequence by means of switching the detector output between the different data channels of a data storage device with the system clock synchronised to the voltage ramp (e.g. an oscilloscope, transient digitiser, multichannel scaler, etc.) driving the tunable filter. Suitable tunable filters are available from Brimrose Corp. Such an apparatus would cost somewhat less to produce than a CCD-based system. Alternatively, the filter could be switched.

The detector may be used to analyse test samples on a solid support, in a cuvette or otherwise. However, the present detector is particularly advantageous when used as the detector in a flow analysis system as described in International Patent WO 97/29376 filed on Feb. 6th, 1997 and claiming a priority date of Feb. 9th, 1996, the contents of which are hereby incorporated by reference, in particular in relation to the types of flow analysis system which may advantageously be adopted. The compositions of the present invention which are soluble in aqueous media are particularly useful in this type of flow analysis system.

EXAMPLE 1

As the absorbance maximum of naphthofluorescein in the presence of a 5% w/v CHAPS is circa 630 nm this can be measured using a 635 nm laser diode as the excitation source. It is also possible to use this endpoint detection system in conjunction with naphthofluorescein phosphate already mentioned above to carry out an assay for alkaline phosphatase as well as immunoassays and enzyme inhibition assays for many analytes e.g. theophylline. Another very application of this approach will be in the area of screening of combinatorially produced compounds for their action on enzymes or receptors implicated in certain disease states.

Results

Figure 13:
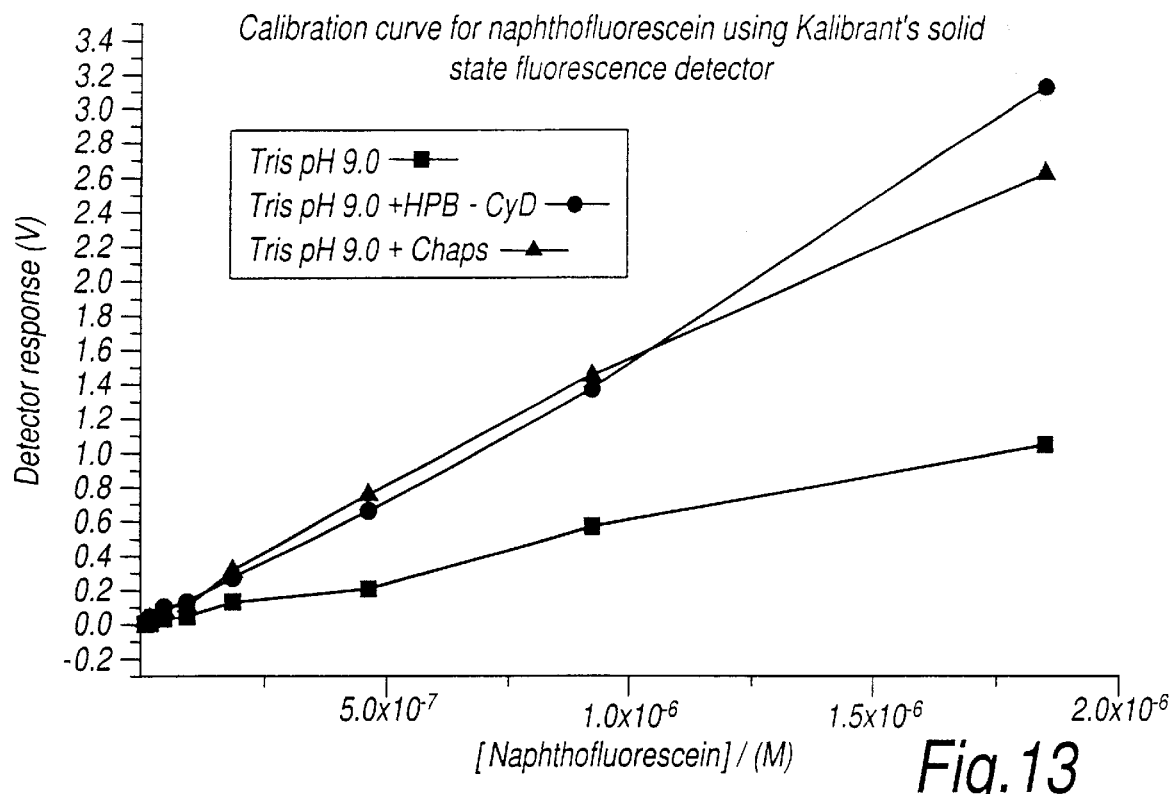
FIG. 13 illustrates a typical calibration curve using solid state fluorescence detector.

The following data was obtained using a portable solid state long wavelength fluorescence detector. The fluorescence detector was constructed using a 2 mW laser diode light source at 635 nm (Power Technology Ltd.), a high speed, large area, silicon photodiode from RS Components Ltd., an Optosigma shortwave cutoff filter (D50.8/WL640) having a transmission of 10% at 635 nm and 88% at 680 nm, a low noise linear amplifier and various construction material. The output from the detector was measured in millivolts using a digital multimeter. The output for naphthofluorescein solutions with and without 2% w/v chaps and hydroxy propyl β-cyclodextrin are shown in FIG. 13.

Exemplary Application

A major activity of pharmaceutical companies is the search for drugs to treat RNA-viruses with long latent periods following infection, such as human immunodeficiency virus (HIV). Reverse transcriptase inhibitors were one of the first group of compounds used successfully to treat AIDS. Initially screening assay were developed to test for the inhibition of this enzyme by a wide range of drug candidates that were developed for the treatment of AIDS. Marimastat a cancer treatment drug under development by British Biotechnology Plc is thought to combat various forms of cancer (e.g. pancreatic cancer) by inhibiting certain metalloprotease enzymes.

It is possible to use the above endpoint detection system in conjunction with naphthofluorescein phosphate already mentioned above and other potential long wavelength enzyme substrates (FIG. 9) to carry out high throughput screening (HTS) of combinatorially produced compounds. The HTS can be in the form of receptor binding assays, ELISAs and enzyme inhibition assays. Another application would be in the use of conventional enzyme substrate assays.

Two screening assay models based on the inhibition of an enzyme by a drug or other analyte are described below using naphthofluorescein. In the first example alkaline phosphatase was the enzyme, naphthofluorescein phosphate the enzyme substrate and theophylline the enzyme inhibitor. In the second example alkaline protease was the enzyme, naphthofluorescein-albumin the conjugate and EDTA the enzyme inhibitor.

An Exemplary Assay Method

Figure 14:
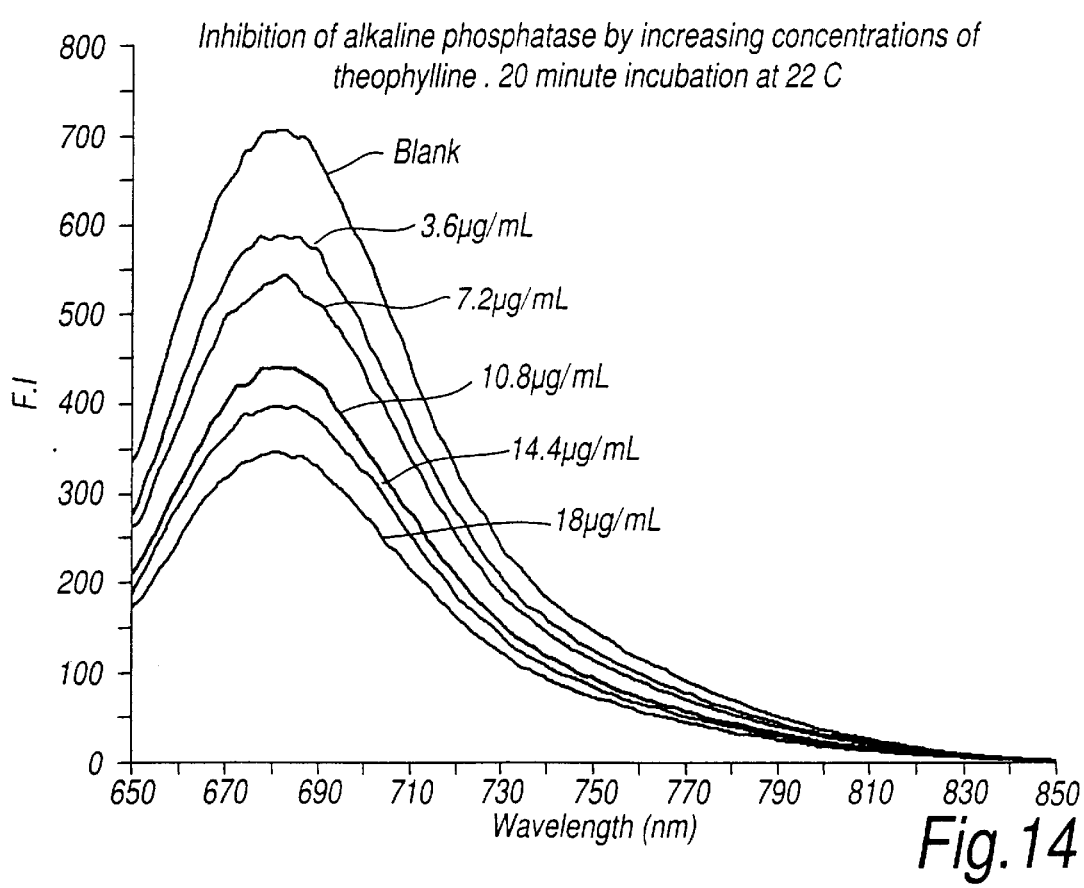
FIG. 14 illustrates inhibition of alkaline phosphatase with increasing concentration of theophylline.
Figure 15:
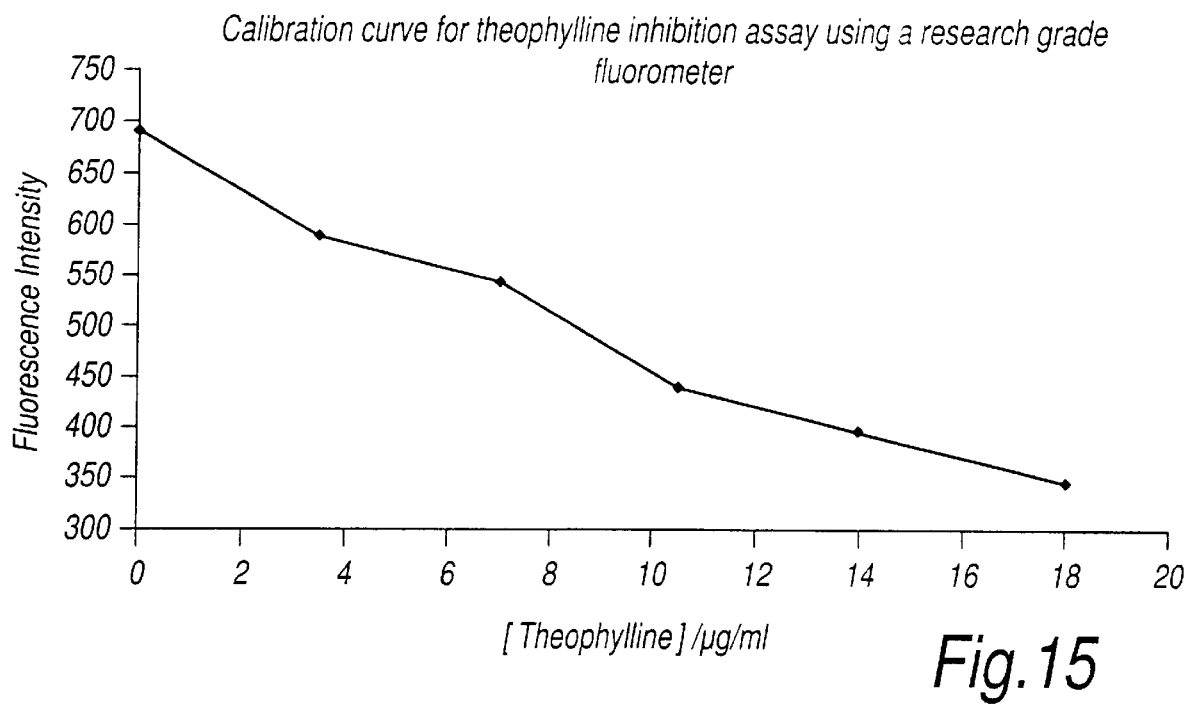
FIG. 15 illustrates a calibration curve for theophylline inhibition assay using research-grade fluorimeter.

100 μl of NFMP (50 μg/ml) was added to 20 μl of alkaline phosphatase (10 μg/ml) and the volume made up to 2 ml with 0.05M Tris buffer pH 9.1 containing 2% w/v CHAPS. The mixture was then incubated at 22° C. for 20 mins. The fluorescence spectra of the hydrolysis product naphthofluorescein was measured using a conventional research fluorimeter over the range 650–840 nm with the excitation monochromator set at 635 nm (i.e. the excitation maxima of naphthofluorescein in the presence of CHAPS). The above procedure was repeated with the inclusion of varying amounts of theophylline over its therapeutic range (0–18 μg/ml) in the incubation mixture. The inhibition of alkaline phosphatase activity by theophylline is shown in FIG. 14. A calibration curve covering the therapeutic range of theophylline is shown in FIG. 15.

Figure 16:
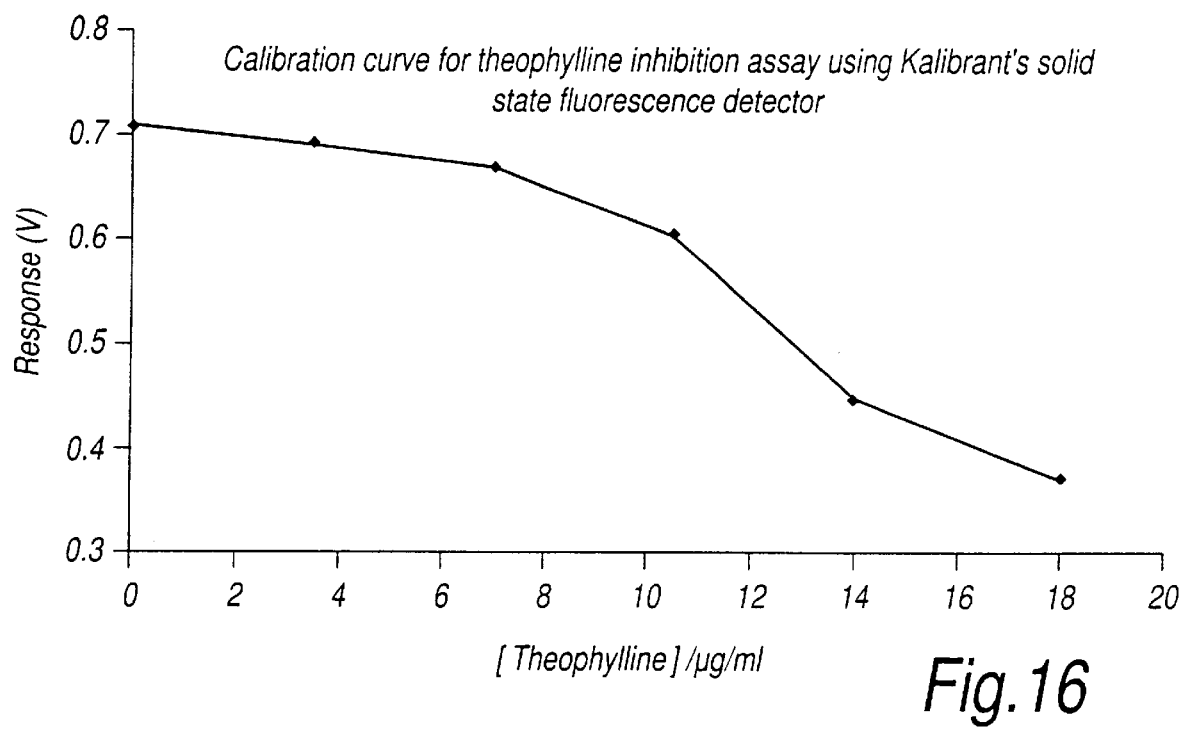
FIG. 16 illustrates a calibration curve for theophylline inhibition assay using solid state fluorimeter.

The above assay was then repeated using the solid state detector described earlier and also in International Application No. PCT/GB98/02394. The results are shown in FIG. 16.

Figure 12:
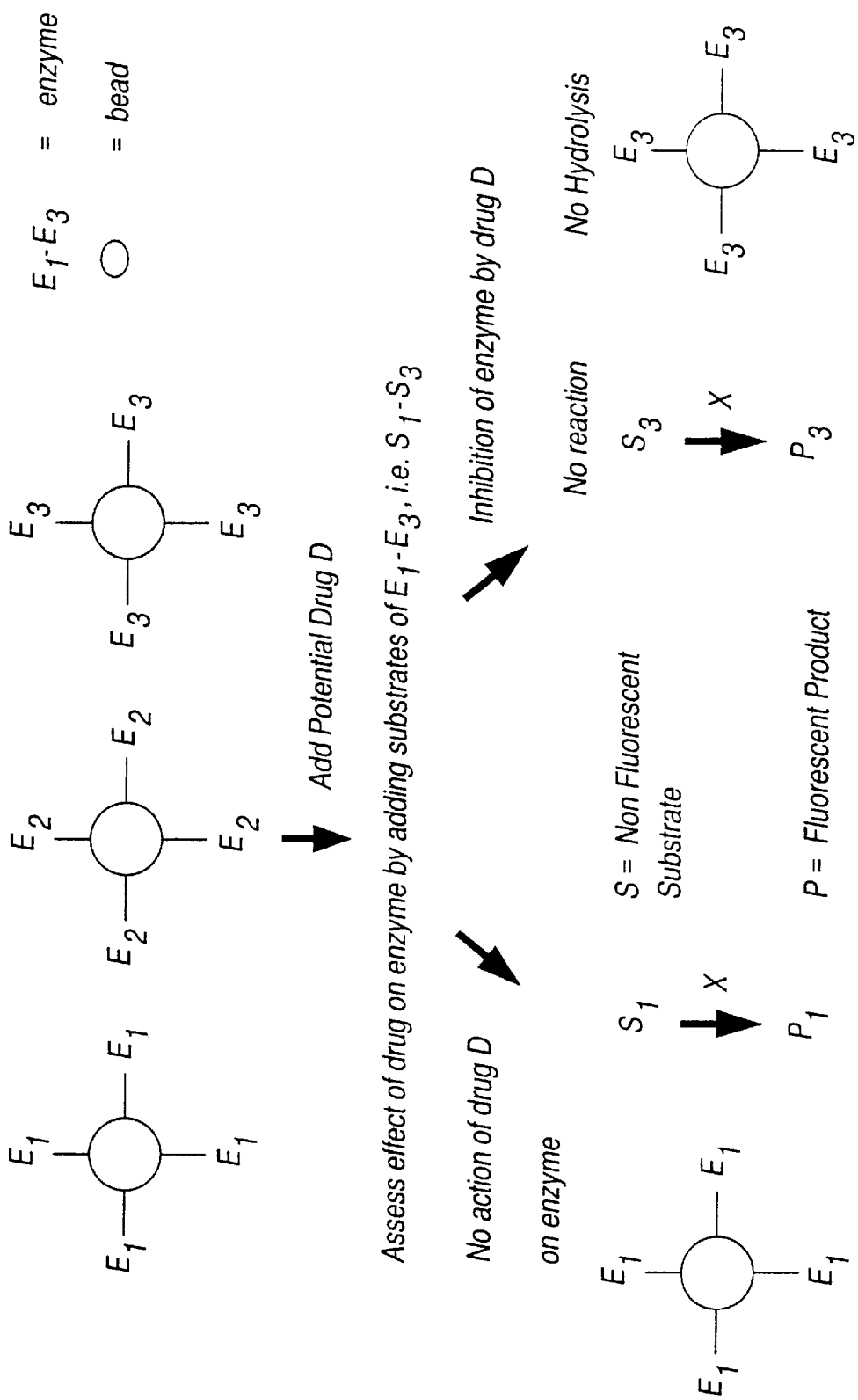
FIG. 12 illustrates the simultaneous screening of multiple targets using the method of the present invention.

This inhibition assay method can be used in a HTS mode for the screening of tens or hundreds of potential drugs against numerous enzymes simultaneously. In it's simplest form a drug produced combinatorially using accurate structure activity relationships (SAR) can be screened against a number of enzymes implicated in different disease states. Each enzyme would have a specific substrate with fluorescence properties similar to naphthofluorescein phosphate e.g. non-fluorescent, but hydrolysable by the specific enzyme to give a long wavelength fluorescent product (excitation/emission maxima greater than 635/680). For example if one drug is screened against four enzymes and each enzyme's hydrolysis product is spectrally resolved from the next, it will be possible to use a slightly modified version of the flow injection multianalyte detection system described in Patent PCT/GB97/00334 and FIG. 17 to screen the drug for inhibitory effects on the four enzymes. The excitation maxima of each enzyme's hydrolysis product must match the operating wavelength of commercially available diode lasers. A typical procedure using the scheme of FIG. 12 and apparatus of FIGS. 17 to 19 will be as follows:

Potential drugs produced combinatorially will be housed in 2 whiles the target molecules immobilised on beads or in solution (e.g. the enzymes) and their substrates will be housed in different compartments within 3. The carrier buffer that is propelled by a peristaltic pump will be housed in 1. Since the target molecules, receptors and enzymes that are implicated in certain disease states are normally in limited supply it is more economical to immobilise these reagents on beads.

The initiation of a screening protocol involving a drug and 4 different enzymes will result in the introduction of a known volume of the potential drug from 2 into the carrier stream. At the same time a known volume of a mixture of the four enzymes immobilised on beads will be introduced into the carrier stream from 3. Both reagents from 2 and 3 will then merge and will be thoroughly mixed in 4. After this interval a known volume of the enzyme specific substrates will be introduced at A from 3 to merge with the drug-enzyme mixture. The resulting potential drug-enzyme-substrate mixture will be incubated for fixed period of time in 5 after which the flow will be diverted to the barrier 6. The enzymatic hydrolysis products which will be fluorescent depending on the effect of the drug will then flow through the barrier 6 to the flow cell 8 and onto the fluorescence detector 9 whilst the beads containing the immobilised enzyme will be retained. These beads will then be back flushed to waste using washing solution from 7. The resulting fluorescence intensities from the enzymatic products will indicate the effect of the potential drug on the particular enzymes investigated. An inhibitory effect of the drug on the enzymes will result in reduced enzyme activity (i.e. little or no fluorescence) whilst the enhancement of enzymatic activities by the drug will result in an increase in the fluorescence signal. Using the above protocol it will be possible to screen a number of enzymes and other target molecules with one or more potential drugs simultaneously as shown diagrammatically in FIG. 12. It is assumed that the enzymes do not interfere with each other and also with the other enzyme substrates.

Currently the reverse procedure is used were thousands or hundreds of thousands of poorly defined potential drugs are screened for activity against one enzyme/receptor at a time. With Kalibrant's technology it will be possible to screen hundreds of well defined potential drugs with or against a group of enzymes implicated in a particular disease or different disease states.

The screening procedure described using naphthofluorescein and naphthofluorescein phosphate could be carried out using 4,10-dibromonaphthofluorescein, vita blue and their corresponding phosphates. The absorbance/excitation maxima of naphthofluorescein and 4,10-dibromonaphthofluorescein was shifted by 40 and 46 nm respectively by CHAPS. It is therefore possible to use a 655 nm laser diode with 4,10-dibromonaphthofluorescein. For example if the absorbance/excitation maxima of vita blue is shifted by an equivalent amount i.e. from 633 nm to about 670 nm it would be possible to use a 670 nm laser diode with this fluorophore. Other naphthofluorescein, 4,10-dibromonaphthofluorescein and vita blue substrates could be used to screened other enzymes e.g. esterases, glycosidases, peptidases/proteases, kinases, sulfatases.

EXAMPLE 2

15 μl of the alkaline protease enzyme (0.57 U/ml) was added to 10 μl of naphthofluorescein-albumin conjugate in carbonate buffer pH 9.6 (conc.) and the volume made up to 1.2 ml with the same buffer. The mixture was then incubated at 37° C. for 10 mins. The increase in fluorescence emission as a result of the hydrolysis of the naphthofluorescein conjugate by the enzyme was monitored at excitation and emission wavelengths of 640 nm and 685 nm respectively (FIG. 4). In another study, inclusion of EDTA in the enzyme and conjugate reaction mixture resulted in the reduced hydrolysis of the substrate by the enzyme. A prototype inhibition assay using the above reagents and EDTA as the inhibitor is shown in FIG. 5. Other enzymes and enzyme inhibitors have been investigated with the naphthofluorescein-albumin conjugates. These include:

a) proteinase K (enzyme), 3-aminophenylboronic acid, monohydrate (proteinase K inhibitor)

b) Chymotrypsin (enzyme), 4-(2-Aminoethyl)-benzenesulfonyl fluoride hydrochloride (chymotrypsin inhibitor).

The assay procedure described in example 2 can be formatted for use in both static and flow based screens. Such formats in particular the flow based approach can be used in HTS of drugs (produced by combinatorial chemistry) for activity against targets e.g. receptors and enzyme.

We claim:

1. A composition comprising a substrate which is a non-fluorescent derivative of a fluorophore, and a shifting reagent which shifts the absorbance wavelength maximum of the fluorophore which maximum is naturally above 450 nm, the shifting reagent being present in an amount predetermined to shift the maximum to a preset value.

2. The composition according to claim 1, wherein the fluorophore is selected from the group consisting of: xanthene dyes; polymethine cyanine dyes; phenoxazine dyes; thiazine dyes; phycobiliproteins; and mixtures thereof.

3. The composition according to claim 2, wherein the fluorophore is selected from the group consisting of:
   a) fluorescein, naphthofluorescein, fluorescent derivatives of fluorescein and naphthofluorescein, anthracene-based dyes;
   b) Cy3, Cy5, Cy7, indocyanine green;
   c) nile blue, nile red, oxazine 750;
   d) methylene blue; and
   e) mixtures thereof.

4. The composition according to claim 1, wherein the shifting reagent is present as a less than 10% w/v solution.

5. The composition according to claim 4, wherein the shifting reagent is present as a less than 5% w/v solution.

6. The composition according to claim 1, wherein the shifting reagent is selected from the group consisting of: cyclodextrins; substituted cyclodextrins; surfactants; detergents; -(3-[(3-cholamidopropyl)dimethylammonio]-1-propane sulphonate (CHAPS); -(3-[(3-cholamidopropyl)dimethylammonio]-2-hydroxy-1-propane sulphonate (CHAPSO); octyl β-glucoside; octyl β-thioglucopyranoside; sodium dodecyl sulphate (SDS); derivatives thereof; albumin; α-Casein; Ovalbumin; and mixtures thereof.

7. The composition according to claim 1, wherein the substrate comprises a derivative of the fluorophore cleavable to the fluorophore.

8. The composition according to claim 7, wherein the derivative cleavable to the fluorophore is chosen from a phosphate, an ester, an imide and an amide derivative of the fluorophore.

9. The composition according to claim 1, further including a second substrate comprising a non-fluorescent derivative of a second fluorophore, wherein the absorbance wavelength maximum of the second fluorophore in the presence of the shifting reagent is different from the absorbance wavelength maximum of the first fluorophore in the presence of the shifting reagent.

10. The composition of claim 9, wherein the absorbance wavelength maximum of the second fluorophore is shifted by the shifting reagent.

11. The composition according to claim 1, comprising a plurality of substrates, wherein the substrates are non-fluorescent derivatives of a plurality of fluorophores, and wherein the absorbance wavelength maximum of each respective fluorophore in the presence of the shifting reagent is different from the absorbance wavelength maximum of the other fluorophores in the presence of the shifting reagent.

12. The composition of claim 11, wherein the absorbance wavelength maximum of one or more of the fluorophores is shifted by the shifting reagent.

13. A method of assaying for a desired product in a sample comprising the steps of:
   a) combining the sample with a substrate and a shifting reagent, the substrate being a non-fluorescent derivative of a fluorophore and the shifting reagent is a reagent which shifts the absorbance wavelength maximum of the fluorophore;
   b) exposing the product of step a to a light source having a maximum intensity at a known excitation wavelength and the shifting agent is used in an amount predetermined to shift the absorbance wavelength maximum of the fluorophore to a value substantially the same as the known excitation wavelength.

14. The method according to claim 13, wherein step a) comprises combining the sample with a plurality of substrates and the shifting reagent, each substrate being a non-fluorescent derivative of a different fluorophore and each fluorophore having a different absorbance wavelength maximum in the presence of the shifting agent; and wherein the light source of step b) has maximum intensity at a plurality of known wavelengths, each of said wavelengths being substantially the same as the absorbance wavelength maximum of one of the plurality of fluorophores.

15. The method according to claim 13, wherein the light source comprises one or more lasers.

16. A method of shifting the absorbance wavelength maximum of a fluorophore in a detection system, comprising exposing a non-fluorescent derivative of said fluorophore to a predetermined amount of a shifting reagent.

17. The method of claim 16, wherein the absorbance wavelength maximum of the fluorophore is shifted to a preset value.

18. A kit for use in a fluorescence assay system, said kit comprising one or more substrates, each substrate being a non-fluorescent derivative of a fluorophore, and a shifting reagent in an amount predetermined to shift the absorbance wavelength maximum of at least one of the fluorophores to a preset value.

19. A kit according to claim 18, wherein each fluorophore has an absorbance wavelength maximum of greater than 450 nM, and wherein the absorbance wavelength maximum of each fluorophore is different when in the presence of the shifting reagent.

* * * * *